(12) United States Patent
Itotani et al.

(10) Patent No.: US 11,582,438 B2
(45) Date of Patent: Feb. 14, 2023

(54) CONTROL DEVICE AND MASTER SLAVE SYSTEM

(71) Applicant: Sony Group Corporation, Tokyo (JP)

(72) Inventors: Yuki Itotani, Tokyo (JP); Kazuki Yokoyama, Tokyo (JP); Koji Aoyama, Tokyo (JP); Atsushi Miyamoto, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 0 days.

(21) Appl. No.: 17/433,237

(22) PCT Filed: Mar. 12, 2020

(86) PCT No.: PCT/JP2020/010797
§ 371 (c)(1),
(2) Date: Aug. 24, 2021

(87) PCT Pub. No.: WO2020/203139
PCT Pub. Date: Oct. 8, 2020

(65) Prior Publication Data
US 2022/0060678 A1    Feb. 24, 2022

(30) Foreign Application Priority Data

Mar. 29, 2019   (JP) .............................. JP2019-067046

(51) Int. Cl.
*H04N 13/296*  (2018.01)
*H04N 13/221*  (2018.01)
(Continued)

(52) U.S. Cl.
CPC .............. *H04N 13/296* (2018.05); *B25J 3/00* (2013.01); *H04N 13/221* (2018.05); *H04N 13/366* (2018.05)

(58) Field of Classification Search
CPC .. H04N 13/296; H04N 13/221; H04N 13/366; B25J 3/00; A61B 90/37;
(Continued)

(56) References Cited

U.S. PATENT DOCUMENTS

2003/0198393 A1   10/2003  Berstis
2008/0297590 A1   12/2008  Barber
(Continued)

FOREIGN PATENT DOCUMENTS

JP    7-253773 A    10/1995
JP    9-147142 A     6/1997
(Continued)

OTHER PUBLICATIONS

Wen Ming-Chang et al: "Teleyes: A telepresence system based on stereoscopic vision and head motion tracking", Automation in Construction, Elsevier, Amsterdam, NL, vol. 89, Feb. 3, 2018 (Feb. 3, 2018).

(Continued)

*Primary Examiner* — Tung T Vo
(74) *Attorney, Agent, or Firm* — Xsensus LLP

(57) ABSTRACT

Provided is a control device including a control unit that calculates a first positional relationship between an eye of an observer observing an object displayed on a display unit and a first point in a master-side three-dimensional coordinate system, and controls an imaging unit that images the object so that a second positional relationship between the imaging unit and a second point corresponding to the first point in a slave-side three-dimensional coordinate system corresponds to the first positional relationship.

12 Claims, 15 Drawing Sheets

(51) Int. Cl.
  *H04N 13/366* (2018.01)
  *B25J 3/00* (2006.01)
(58) Field of Classification Search
  CPC ...... A61B 2034/2055; A61B 2034/741; A61B 2034/742; A61B 2090/064; A61B 34/37
  USPC .......................................................... 348/50
  See application file for complete search history.

(56) References Cited

U.S. PATENT DOCUMENTS

| | | | | |
|---|---|---|---|---|
| 2011/0118748 | A1* | 5/2011 | Itkowitz | A61B 34/30 606/130 |
| 2011/0118752 | A1* | 5/2011 | Itkowitz | A61B 34/30 345/157 |
| 2011/0118753 | A1* | 5/2011 | Itkowitz | A61B 34/37 606/130 |
| 2012/0071891 | A1* | 3/2012 | Itkowitz | G05B 15/02 715/863 |
| 2012/0071892 | A1* | 3/2012 | Itkowitz | B25J 13/086 606/130 |
| 2016/0314716 | A1* | 10/2016 | Grubbs | G09B 23/306 |
| 2016/0314717 | A1* | 10/2016 | Grubbs | G09B 23/32 |
| 2017/0042730 | A1* | 2/2017 | He | A61B 34/30 |
| 2017/0143442 | A1* | 5/2017 | Tesar | H04N 13/344 |
| 2017/0172675 | A1 | 6/2017 | Jarc | |
| 2018/0368656 | A1* | 12/2018 | Austin | A61B 90/361 |
| 2019/0254759 | A1* | 8/2019 | Azizian | A61B 34/35 |
| 2019/0282312 | A1* | 9/2019 | Nowlin | A61B 34/20 |
| 2020/0005679 | A1* | 1/2020 | Grubbs | G09B 23/28 |
| 2020/0405403 | A1* | 12/2020 | Shelton, IV | A61B 17/3417 |

FOREIGN PATENT DOCUMENTS

| | | |
|---|---|---|
| JP | 2004-213673 A | 7/2004 |
| WO | 2017/094844 A1 | 6/2017 |
| WO | WO-2017210101 A1 | 12/2017 |

OTHER PUBLICATIONS

Zhu D et al:"""Moving to the centre":AI 1-13gaze-driven remote camera control for teleoperation", Interacting With Computers, Butterworth-Heinemann, GB, vol. 23, No. 1, Jan. 1, 2011 (Jan. 1, 2011).

International Search Report and Written Opinion dated Jun. 16, 2020, received for PCT Application PCT/JP2020/010797, Filed on Mar. 12, 2020, 8 pages including English Translation.

* cited by examiner

FIG. 8
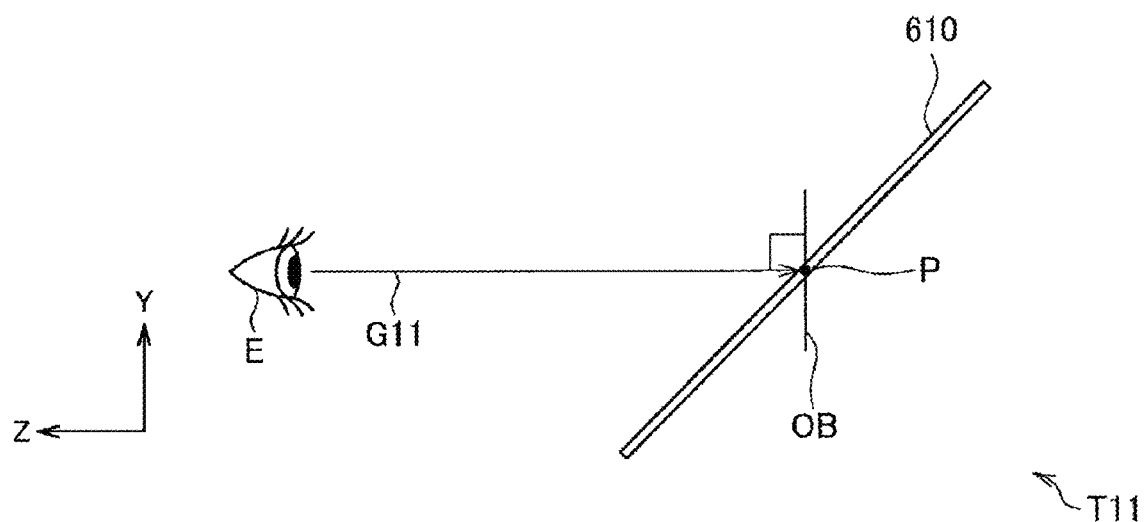
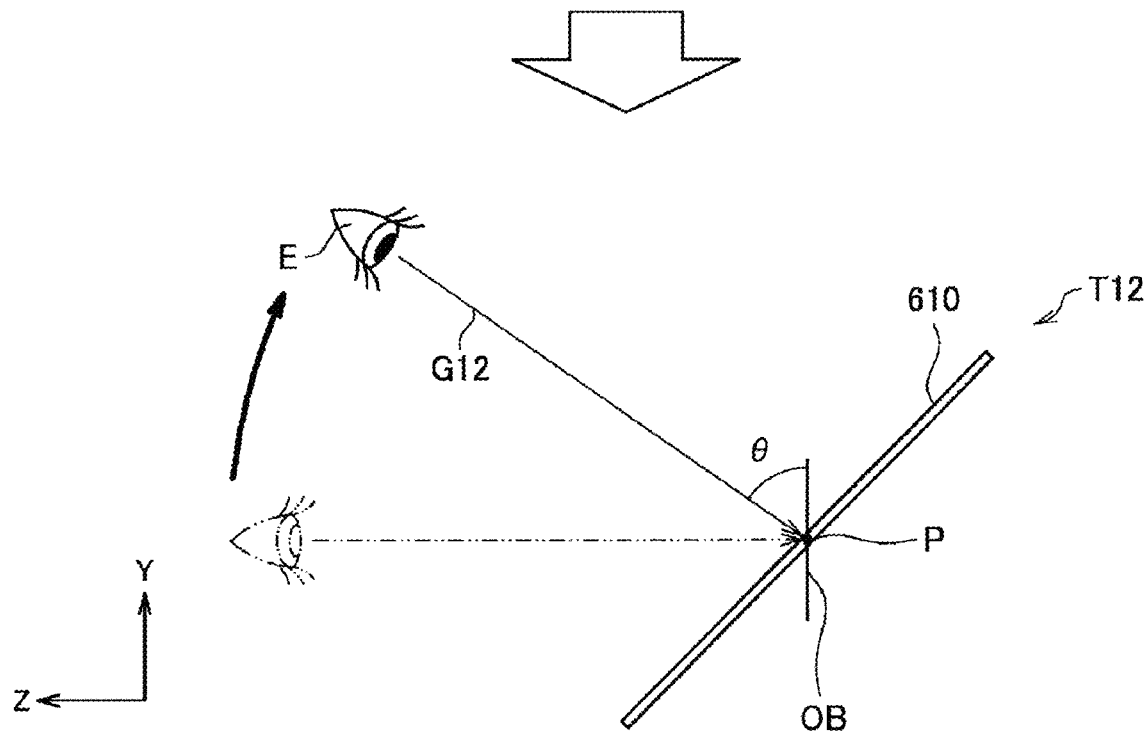

FIG. 9
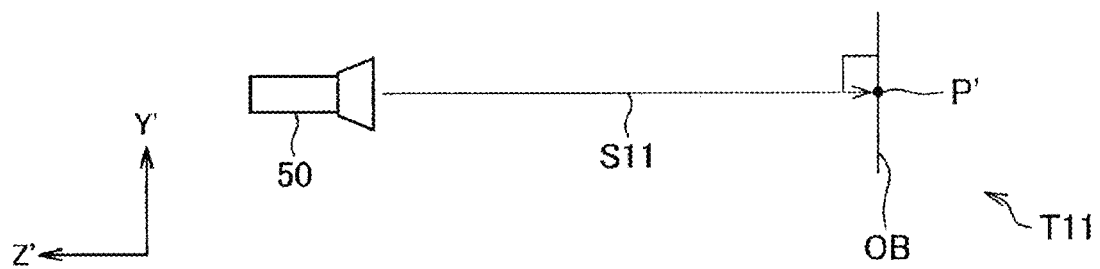
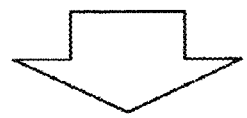
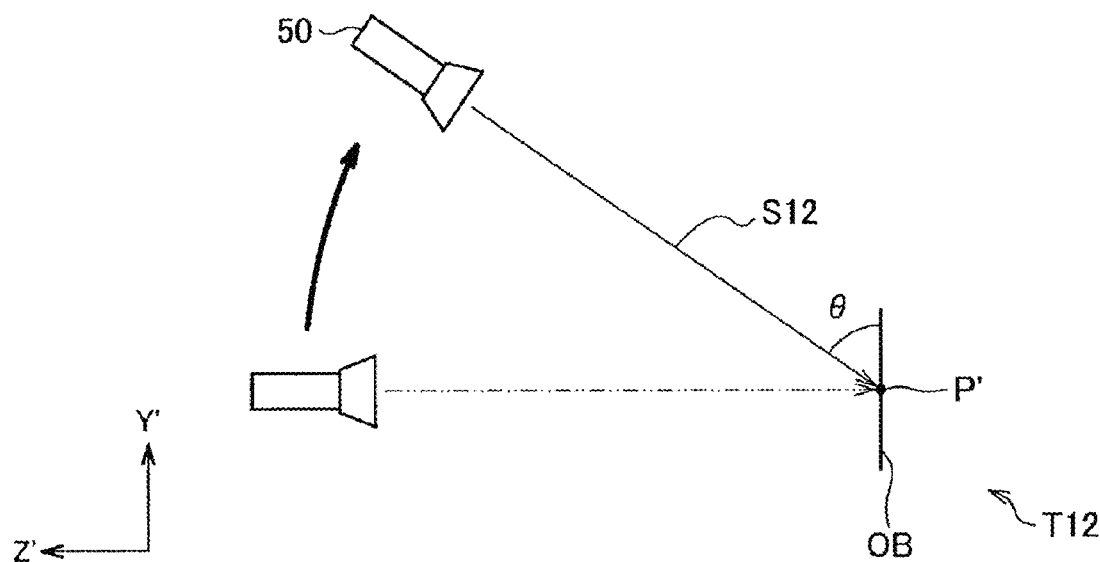

FIG. 11
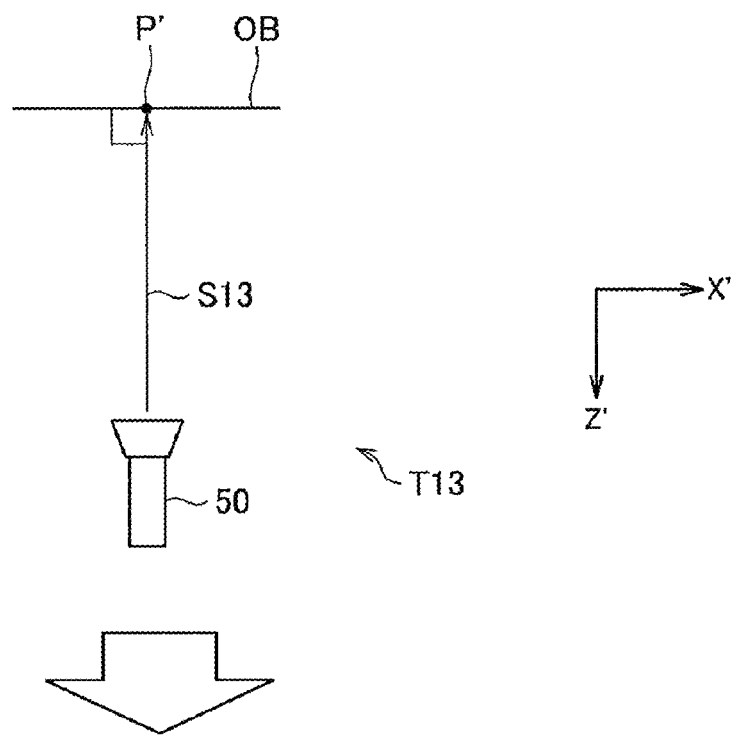
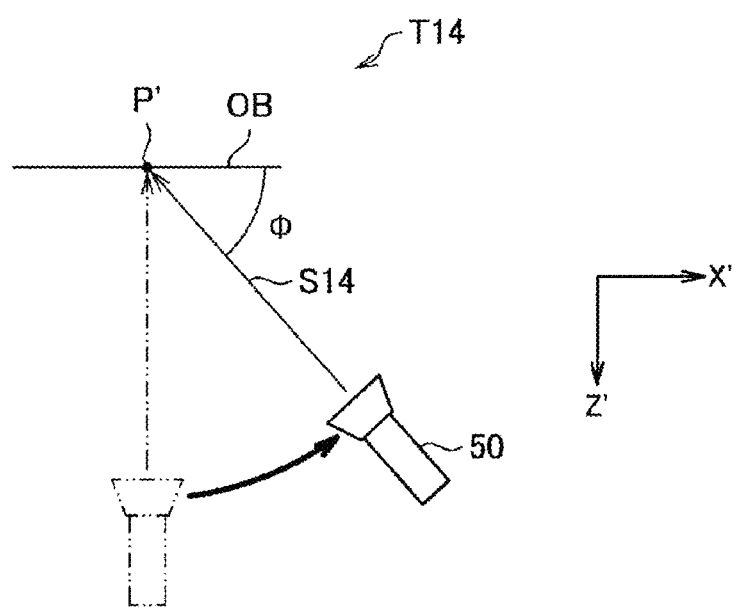

FIG. 12
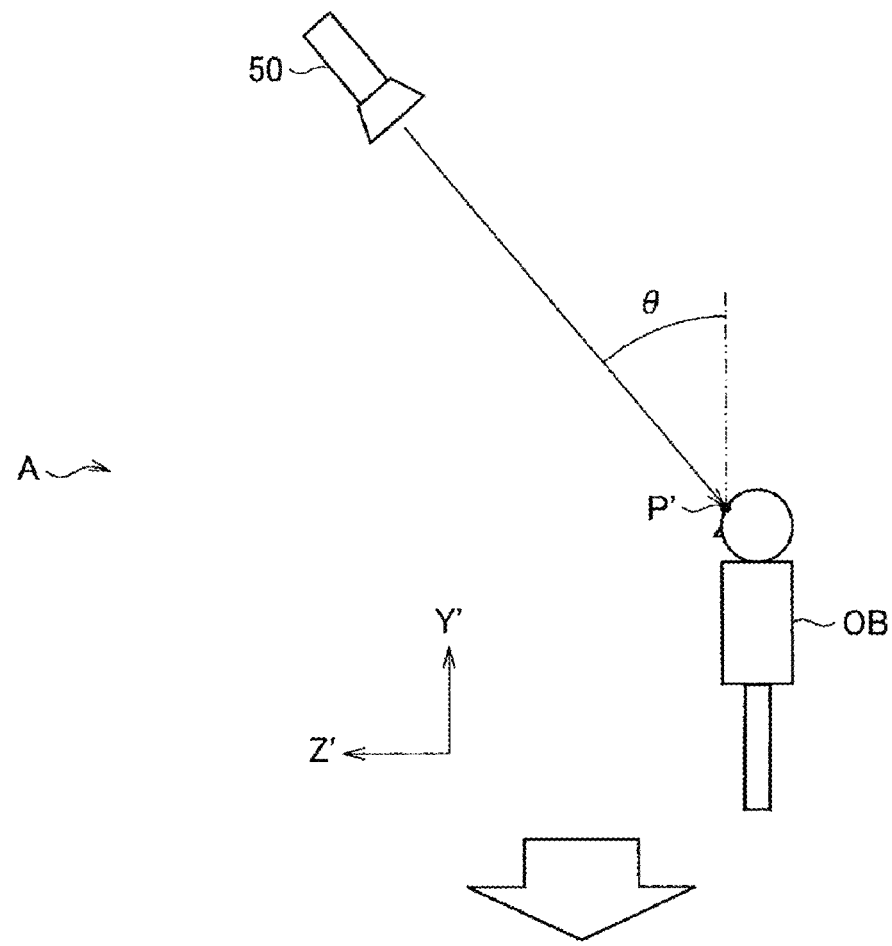
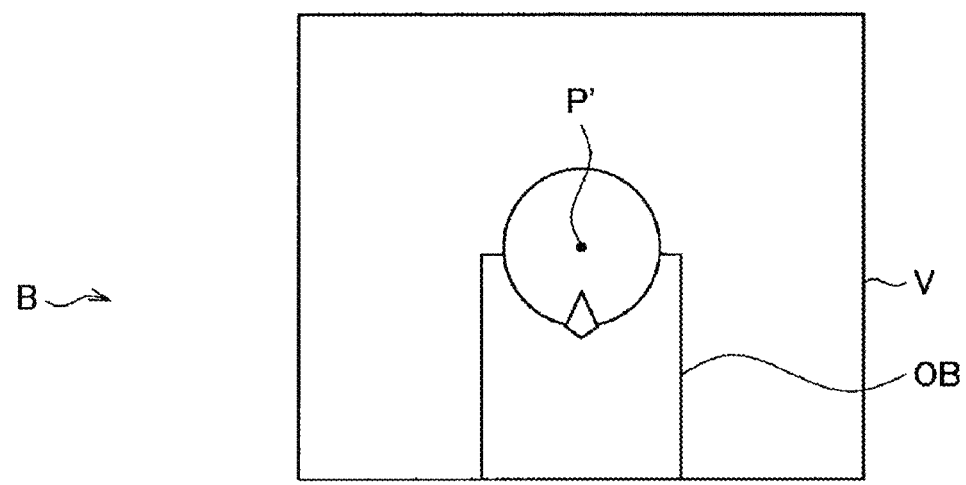

CONTROL DEVICE AND MASTER SLAVE SYSTEM

CROSS-REFERENCE TO RELATED APPLICATIONS

The present application is based on PCT filing PCT/JP2020/010797, filed Mar. 12, 2020, which claims priority to JP 2019-067046, filed Mar. 29, 2019, the entire contents of each are incorporated herein by reference.

TECHNICAL FIELD

The present disclosure relates to a control device and a master slave system.

BACKGROUND ART

In recent years, as a surgical system used for performing endoscopic surgery or the like, a master slave system (hereinafter, also referred to as a master slave system) that enables approach to an affected part without making a large incision in a patient's body has been known. In such a master slave system, an operator (user) such as a doctor operates a master unit including the input interface, and a slave unit including a medical instrument such as forceps, tweezers, or an endoscope is remotely operated in accordance with the operation of the master unit by the operator. The slave unit is configured as, for example, an arm device in which a surgical tool is held at the distal end, and can change the position or posture of the surgical tool in the abdominal cavity.

Regarding a master slave system, a method of presenting an image to a user (observer) for enabling an intuitive operation of a slave unit has been studied. For example, Patent Document 1 below discloses a technique for controlling the position and posture of a slave-side camera on the basis of the position and posture of a head mounted display worn by a user.

CITATION LIST

Patent Document

Patent Document 1: Japanese Patent Application Laid-Open No. 2004-213673

SUMMARY OF THE INVENTION

Problems to be Solved by the Invention

However, depending on various technologies such as Patent Document 1, there has been a possibility that the user (observer) cannot intuitively observe the object in the master slave system. For example, depending on a technique or the like for translating the slave-side camera in accordance with the direction of the face of the master-side user, the user cannot observe the object as if looking around from various directions of up, down, left, and right of the object, so that it cannot be said that intuitiveness is sufficient.

Therefore, the present disclosure has been made in view of the above circumstances, and provides a novel and improved control device and master slave system that enable a user (observer) to more intuitively observe an object in the master slave system.

Solutions to Problems

According to the present disclosure, there is provided a control device including a control unit that calculates a first positional relationship between an eye of an observer observing an object displayed on a display unit and a first point in a master-side three-dimensional coordinate system, and controls an imaging unit that images the object so that a second positional relationship between the imaging unit and a second point corresponding to the first point in a slave-side three-dimensional coordinate system corresponds to the first positional relationship.

Furthermore, according to the present disclosure, provided is a master slave system including a slave unit, a master unit used to operate the slave unit, and a control unit that calculates a first positional relationship between an eye of an observer observing an object displayed on a display unit and a first point in a master-side three-dimensional coordinate system, and controls an imaging unit that images the object so that a second positional relationship between the imaging unit and a second point corresponding to the first point in a slave-side three-dimensional coordinate system corresponds to the first positional relationship.

BRIEF DESCRIPTION OF DRAWINGS

FIG. 8 is a diagram when a state in which a user looks at an object displayed on a display surface is viewed from a lateral direction (in a direction opposite to an X-axis direction).

FIG. 9 is a diagram when a state in which an imaging unit images an object is viewed from a lateral direction (in a direction opposite to an X'-axis direction).

FIG. 11 is a diagram when a state in which an imaging unit is imaging an object is viewed from above (in a direction opposite to a Y'-axis direction).

FIG. 12 is a diagram for explaining a coping method in a case where an angle of a first observation direction with respect to a gravity direction is different from an angle of a second observation direction with respect to the gravity direction.

MODE FOR CARRYING OUT THE INVENTION

Figure 1:
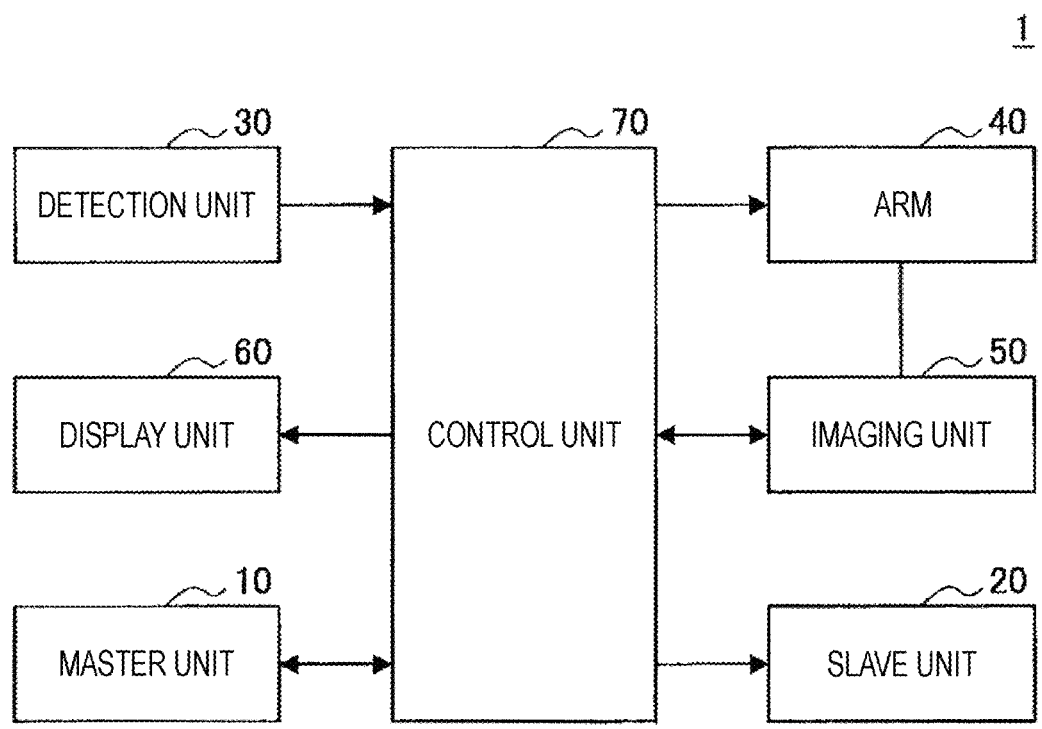
FIG. 1 is a block diagram illustrating a configuration example of a master slave system according to the present embodiment.

Hereinafter, preferred embodiments of the present disclosure will be described in detail with reference to the accompanying drawings. Note that, in the present specification and the drawings, components having substantially the same functional configuration are denoted by the same reference numerals, and redundant description is omitted.

Note that the description will be given in the following order.

1. Background
2. Embodiments
2.1. System configuration example
2.2. Control example by control unit
2.3. Configuration example of control unit
2.4. Processing flow example of each configuration
2.5. Hardware configuration example of control unit
3. Conclusion

1. BACKGROUND

Before describing an embodiment of the present disclosure, first, a background in which the embodiment of the present disclosure has been created will be described.

As described above, in recent years, the master slave system has been used in the field of endoscopic surgery and the like. Then, as for the master slave system, a method of presenting an image to a user (observer) for enabling an intuitive operation of a slave unit as in the technique described in Patent Document 1 described above has been studied.

However, depending on various technologies such as Patent Document 1, there is a case where the observer cannot intuitively observe the object in the master slave system. For example, depending on a technique or the like for translating the slave-side camera in accordance with the direction of the face of the master-side user, the user cannot observe the object as if looking around from various directions of up, down, left, and right of the object, so that it cannot be said that intuitiveness is sufficient.

The present discloser has created the technology according to the present disclosure in view of the above circumstances. A control device according to an embodiment of the present disclosure calculates a first positional relationship between an eye of a user (observer) observing an object displayed on a display unit (for example, display) and a first point in a master-side three-dimensional coordinate system, and controls an imaging unit (for example, camera) that images the object so that a second positional relationship between the imaging unit and a second point corresponding to the first point in a slave-side three-dimensional coordinate system corresponds to the first positional relationship. For example, the control device according to the present embodiment acquires information regarding the first observation direction of the eye of the user with respect to the first point in the master-side three-dimensional coordinate system, and controls the second observation direction so that the second observation direction of the imaging unit 50 with respect to the second point in the slave-side three-dimensional coordinate system corresponds to the first observation direction.

As a result, the user can observe the object to look around from various directions of up, down, left, and right of the object by changing the position of the eye, so that the user can more intuitively observe the object.

Furthermore, studies have been conducted on how to acquire an image and provide the image to a user to enable more intuitive operation in the master slave system. For example, when the master unit and the slave unit are perceived to move in parallel, the user can intuitively perform an operation. On the contrary, when the master unit and the slave unit are perceived to move in different directions, the user needs to perform an operation while considering the relationship between the motion directions of the master unit and the slave unit, which makes it difficult to perform an intuitive operation. This event is called "Mental Rotation". The control device according to the present embodiment achieves an intuitive operation by performing control so as not to generate the Mental Rotation.

Hereinafter, control by the control device according to the present embodiment will be described in detail.

2. EMBODIMENT (2.1. System Configuration Example)

The background that led to the creation of the present embodiment has been described above. Next, a configuration example of a master slave system 1 according to the present embodiment will be described. Note that the description will be given assuming that the master slave system 1 according to the present embodiment is a surgical system used for endoscopic surgery or the like, but the type of the master slave system 1 is not particularly limited. For example, the master slave system 1 may be a robot control system that remotely controls a robot.

FIG. 1 is a block diagram illustrating a configuration example of the master slave system 1 according to the present embodiment. As illustrated in FIG. 1, the master slave system 1 includes a master unit 10, a slave unit 20, a detection unit 30, an arm 40, an imaging unit 50, a display unit 60, and a control unit 70. Note that the control device according to the present embodiment is only required to include at least the control unit 70 in the above configuration.

The master unit 10 is a master-side device in the master slave system 1. The master unit 10 can be a manipulator (robot having a link mechanism including a passive joint) having one or two or more joints including a passive joint and a link connected to the joint, and is used for operating the slave unit 20.

Figure 2:
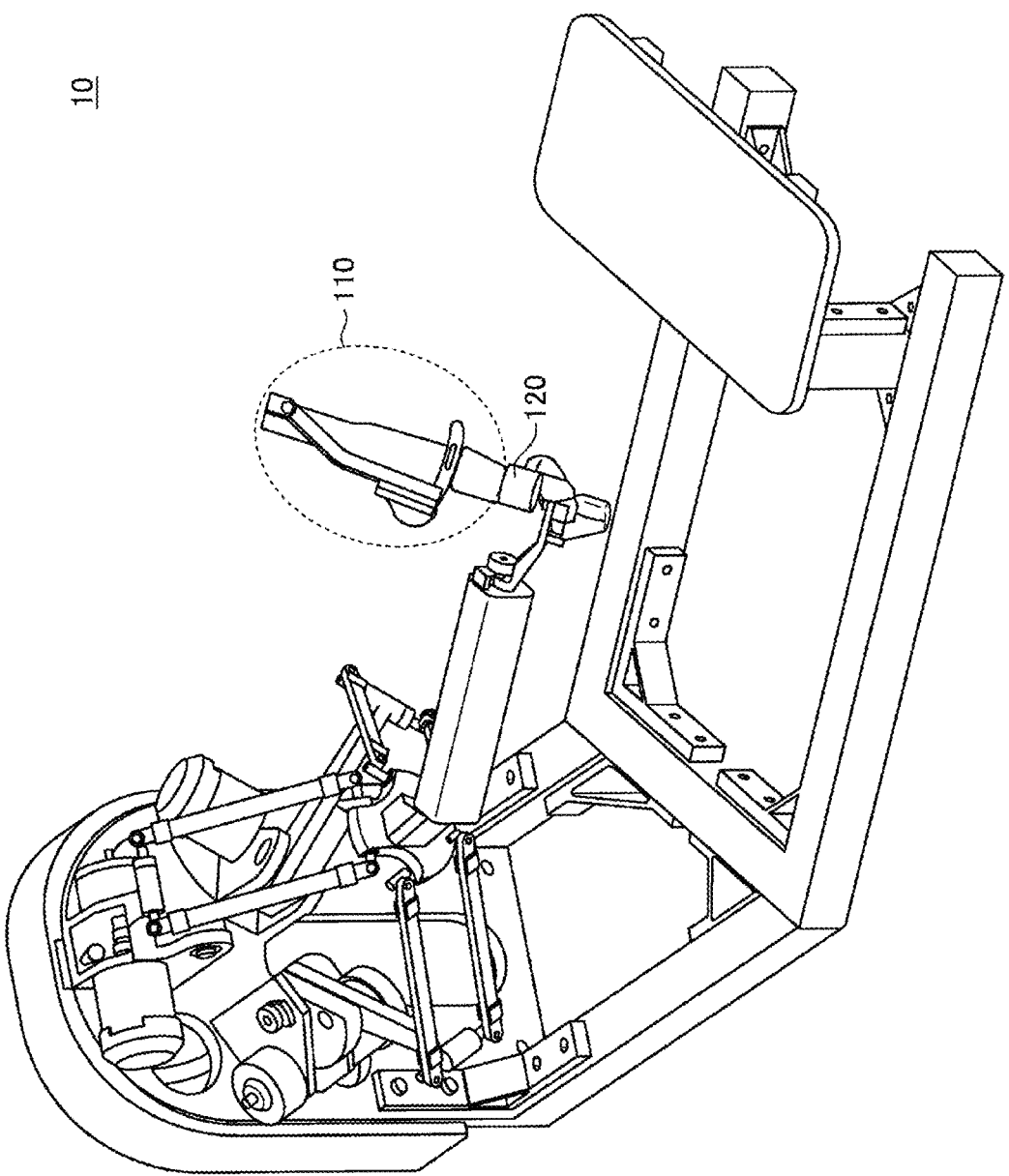
FIG. 2 is a view illustrating an example of a master unit according to the present embodiment.

FIG. 2 is a view illustrating an example of the master unit 10 according to the present embodiment. In the example illustrated in FIG. 2, the master unit 10 includes an operation body 110 provided on a link connected to a passive joint and a force sensor 120 that measures a force applied to the operation body 110. Here, examples of the force sensor 120 according to the present embodiment include any sensor capable of measuring the force applied to the operation body 110, such as "any type of force sensor such as a type using a strain gauge" and "any type of tactile sensor such as a type that obtains a tactile sense by measuring vibration with a piezoelectric element, a microphone, or the like". Furthermore, the master unit 10 includes, for example, a motion sensor for measuring the motion of the joint at a position corresponding to each joint.

In the present embodiment, the operation body 110 is an input interface of the master unit 10, and the user can move (remotely operate) the position of the slave unit 20 by an operation of moving the position of the operation body 110.

Note that FIG. 2 illustrates an example in which the operation body 110 provided in the master unit 10 is a stylus type operation device, but the operation body 110 according to the present embodiment is not limited to the example illustrated in FIG. 2. Examples of the operation body 110 according to the present embodiment include an operation device having any shape such as a glove type operation device. Furthermore, the operation body 110 according to the present embodiment may be any operation device applicable to a haptic device. Furthermore, the master unit 10 may have a structure in which the operation body 110 can be replaced. Note that the configuration of the master unit 10 according to the present embodiment is not limited to the example illustrated in FIG. 2, and may be any configuration.

The slave unit 20 is a slave-side device in the master slave system 1. The slave unit 20 may be a manipulator (robot having a link mechanism including an active joint) having one or two or more active joints and a link connected to the active joint for moving in response to an input operation to the master unit 10. Furthermore, the slave unit 20 includes, for example, a drive mechanism for driving the active joint at a position corresponding to each of the active joints. Examples of the drive mechanism include a motor and a driver. Such a drive mechanism can be controlled by the control unit 70 described later.

Figure 3:
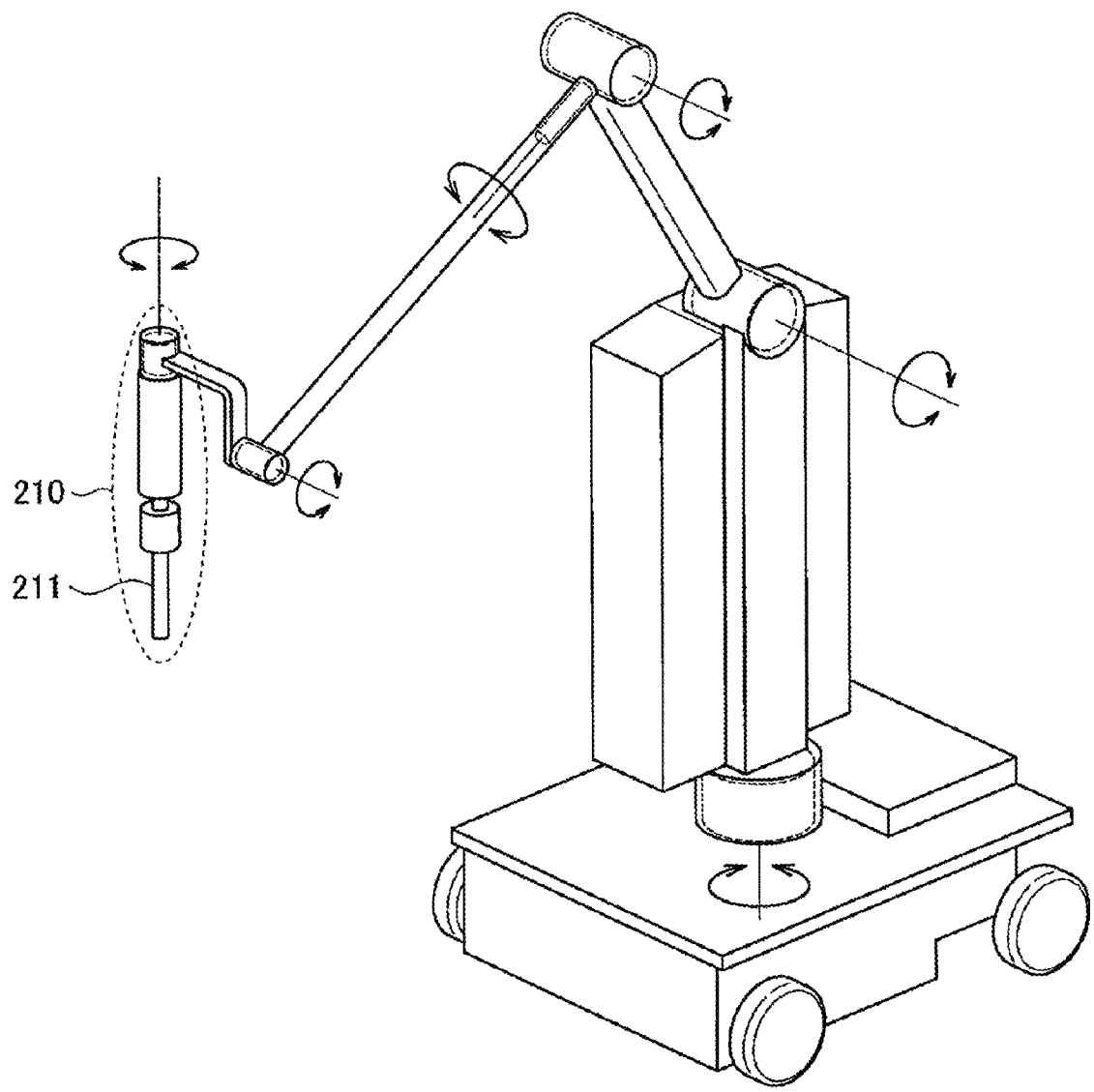
FIG. 3 is a view illustrating an example of a slave unit according to the present embodiment.

FIG. 3 is a view illustrating an example of the slave unit 20 according to the present embodiment. In the example illustrated in FIG. 3, the distal end portion 210 which is the distal end portion of the arm of the slave unit 20 includes a contact portion 211 where the surgical tool comes into contact with the patient, and the user remotely controls the position of the contact portion 211 by operating the master unit 10. Note that FIG. 3 illustrates an example, and the configuration of the slave unit 20 according to the present embodiment is not limited to the example of FIG. 3. Furthermore, in the present embodiment, it is assumed that the slave unit 20 is a real object (that is, the space on the slave side is the real space), but the present invention is not necessarily limited thereto, and the slave unit 20 may be a virtual object (that is, the space on the slave side is the virtual space). For example, the present disclosure may be applied to a surgery simulator or the like, and the slave unit 20 that is a virtual object may be controlled by the operation of the master unit 10.

The detection unit 30 is configured to detect an eye of a user (observer). For example, the detection unit 30 has an imaging function, and can detect the eye of the user appearing in the image by analyzing the image acquired by imaging. At this time, a tracker (a device for tracking the user's eye), a marker (a mark for detecting the user's eye), or the like may be attached near the user's eye so that the user's eye can be accurately detected (for example, a user wears an eyeglass-type device to which a tracker or a marker is attached.). Note that the method of detecting the user's eye by the detection unit 30 is not necessarily limited thereto. Furthermore, the target detected by the detection unit 30 may be the one equivalent to the eye (for example, a point near the eye, or the like). In a case where the user's eye is detected, the detection unit 30 provides the control unit 70 with information (hereinafter, referred to as detection information) capable of specifying the position of the eye in the master-side three-dimensional coordinate system. The detection information may be, for example, position coordinates of the eye in the master-side three-dimensional coordinate system.

The arm 40 supports the imaging unit 50 and has a configuration capable of controlling the position and posture of the imaging unit 50. For example, the arm 40 can be a manipulator (robot having a link mechanism including an active joint) having one or two or more joints including an active joint and a link connected to the active joint, and can be controlled by the control unit 70 described later.

The imaging unit 50 is configured to acquire an image of an affected part by imaging. The imaging unit 50 is assumed to be a stereo camera capable of acquiring a stereoscopic image, but is not necessarily limited thereto, and may be, for example, an endoscope or the like. The imaging unit 50 according to the present embodiment may include a zoom mechanism and be capable of changing the imaging magnification (zoom magnification). Furthermore, as described above, the imaging unit 50 is supported by the arm 40, and the position and posture of the imaging unit 50 are changed by controlling the angle of the joint of the arm 40 and the like. The imaging processing by the imaging unit 50 can be controlled by the control unit 70 described later.

The display unit 60 is configured to display a stereoscopic image on the basis of control by the control unit 70 described later. For example, the display unit 60 may be a stereoscopic display capable of displaying a stereoscopic image. Furthermore, the display unit 60 is assumed to be mounted on a stationary device (that is, the positional relationship between the user's eye and the image displayed on the display unit 60 changes depending on the position and posture of the user). When the display unit 60 is mounted on a stationary device, for example, as in a case where the display unit 60 is mounted on a head mounted display, a problem that a stereoscopic image cannot be shared by a plurality of people and a problem that a view is blocked by a display are solved.

The control unit 70 is configured to control each of the other components included in the master slave system 1. The control unit 70 is connected to each of the other components included in the master slave system 1 by any communication method. For example, the control unit 70 receives information measured by a sensor included in the master unit 10 from the master unit 10, and acquires the designated position of the master unit 10 on the basis of the received information. Then, the control unit 70 controls the designated position (for example, the position of the contact portion 211) of the slave unit 20 on the basis of the designated position of the master unit 10, an offset (details will be described later), and the like. Here, the "designated position of the master unit 10" is a position determined by the master unit 10, and can be, for example, a position (of the master unit 10) designated by the user inputting to the master unit 10. Furthermore, the "designated position of the slave unit 20" is a position determined by the designated position of the master unit 10, and can be, for example, a position (of the slave unit 20) designated by the user inputting to the master unit 10. That is, the position of the slave unit 20 can be determined on the master slave system 1 by the user operating the master unit 10. Note that the "designated position" is not necessarily limited to a position designated by the intention of the user. For example, the "designated position of the master unit 10" may be a position simply determined by the position of the master unit 10 (the same applies to the "designated position of the slave unit 20").

Furthermore, the control unit 70 according to the present embodiment performs control for achieving intuitive observation and intuitive operation by the user. Hereinafter, the control by the control unit 70 will be described in detail.

Note that the configuration illustrated in FIG. 1 is merely an example, and the configuration example of the master slave system 1 according to the present embodiment is not necessarily limited to the example of FIG. 1. For example, a voice acquisition unit (for example, a stereo microphone) may be provided on the slave side, and a voice output unit (for example, a speaker, an earphone, or the like) that outputs the slave-side voice acquired by the voice acquisition unit may be provided on the master side. Furthermore, with these configurations, the sound field on the slave side may be reproduced on the master side.

(2.2. Control Example by Control Unit)

The configuration example of the master slave system 1 according to the present embodiment has been described above. Next, a control example by the control unit 70 according to the present embodiment will be described.

(Object Display Control)

First, object display control will be described.

In a case where the stereoscopic display is provided to the user as in the present embodiment, in order to enhance the stereoscopic feeling felt by the user and the feeling as if the object exists in the same space (hereinafter, also referred to as a feeling of coexistence), for example, it is desirable to increase the parallax amount caused by the displacement in the horizontal direction of the image visually recognized by the right eye and the image visually recognized by the left eye.

FIGS. 4 to 7 are explanatory diagrams illustrating an example of stereoscopic display by the display unit 60 according to the present embodiment. The control unit 70 can cause the object to be displayed on the display unit 60 in various modes illustrated in FIGS. 4 to 7.

Figure 4:
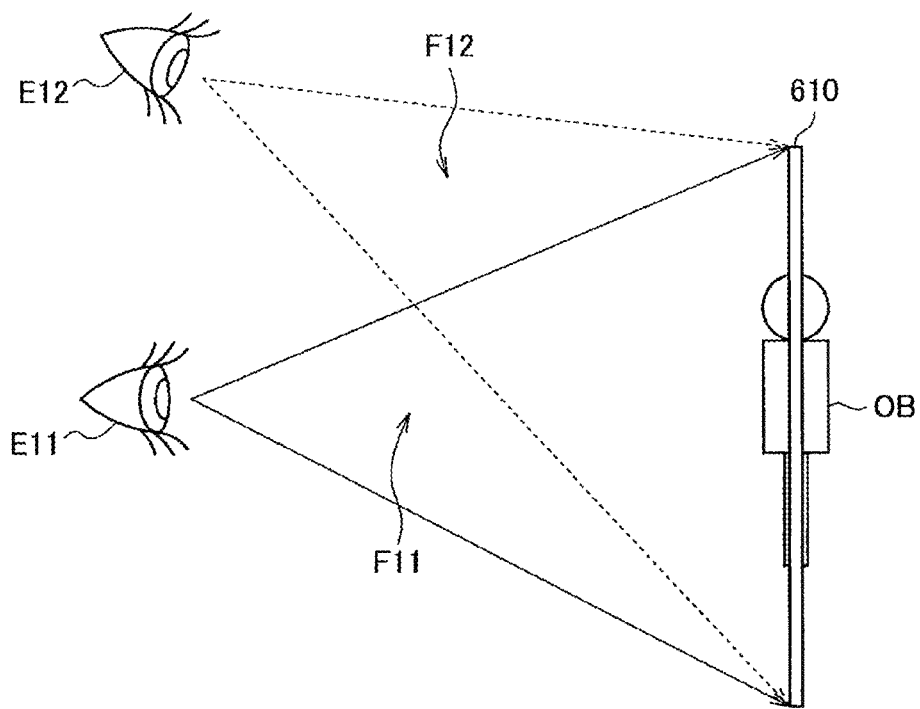
FIG. 4 is an explanatory diagram illustrating an example of stereoscopic display by a display unit according to the present embodiment.

For example, in the example illustrated in FIG. 4, a stereoscopic object OB is displayed in the vicinity of the display surface 610 of the display unit 60. In the example illustrated in FIG. 4, the object OB is included in a field of view F11 when the user observes from a viewpoint E11, and the object OB is included in a field of view F12 when the user observes from a viewpoint E12. In the example illustrated in FIG. 5, the object OB is arranged on the front side of the display surface 610 of the display unit 60. In the example illustrated in FIG. 5, the object OB is included in a field of view F21 when the user observes from a viewpoint E21, and the upper portion of the object OB is included in a field of view F22 when the user observes from a viewpoint E22. In the example illustrated in FIG. 6, the object OB is arranged on the back side of the display surface 610 of the display unit 60. In the example illustrated in FIG. 6, the object OB is included in a field of view F31 when the user observes the object OB from a viewpoint E31. On the other hand, when the user observes the object OB from a viewpoint E32, the object OB is displayed on the back side of the display surface 610 even though the field of view of the user is a range in which a field of view F32 and a field of view F33 are combined, and thus, the field of view for the user to observe the object OB is limited to the field of view F32.

Figure 5:
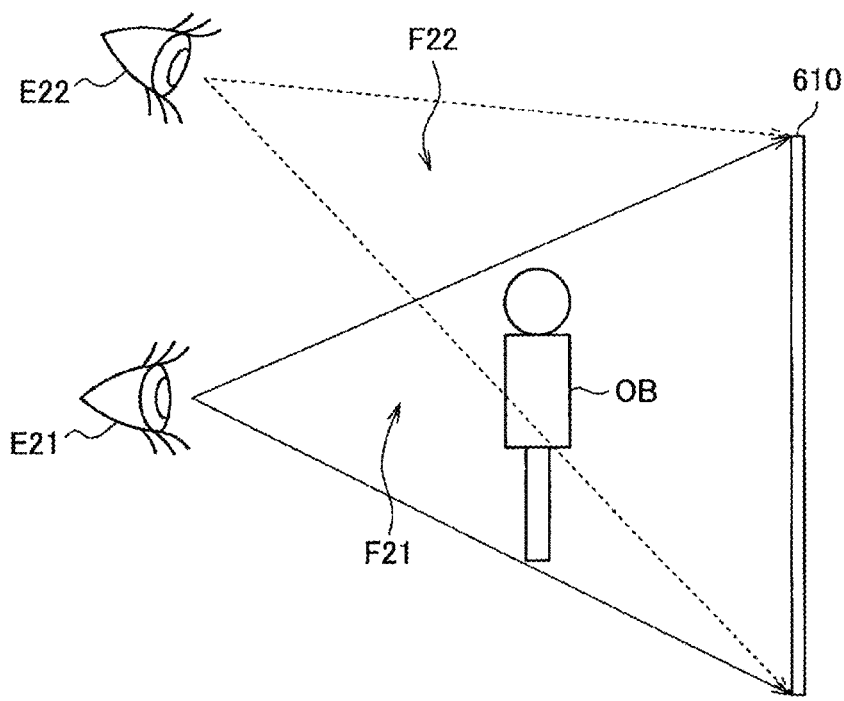
FIG. 5 is an explanatory diagram illustrating an example of stereoscopic display by the display unit according to the present embodiment.
Figure 6:
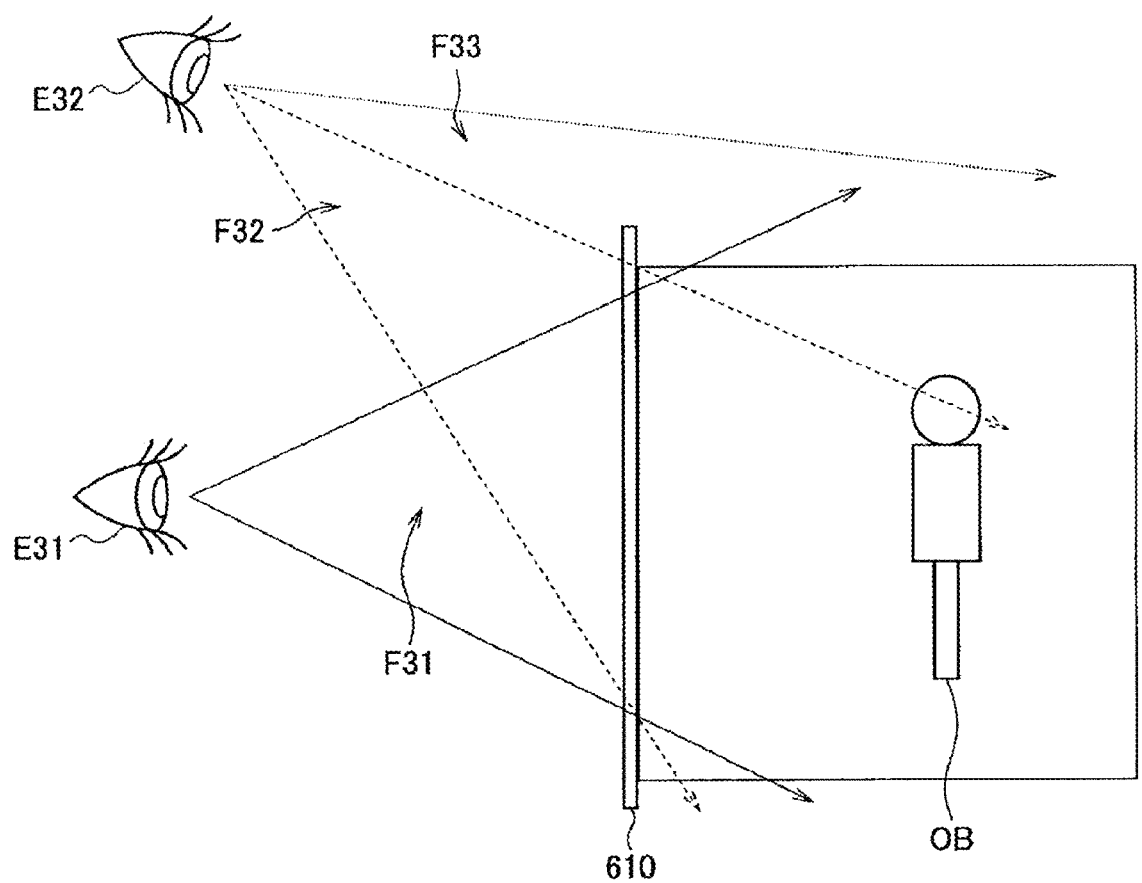
FIG. 6 is an explanatory diagram illustrating an example of stereoscopic display by the display unit according to the present embodiment.

In the examples illustrated in FIGS. 4 to 6, the display unit 60 is installed so that the display surface 610 of the display unit 60 is perpendicular to the horizontal plane in the real space. On the other hand, in the example illustrated in FIG. 7, the display unit 60 is installed so that the display surface 610 of the display unit 60 is inclined (non-perpendicular) to the horizontal plane in the real space. Furthermore, in the example illustrated in FIG. 7, the object OB is arranged so as to intersect the display surface 610 while standing upright with respect to the horizontal plane.

Figure 7:
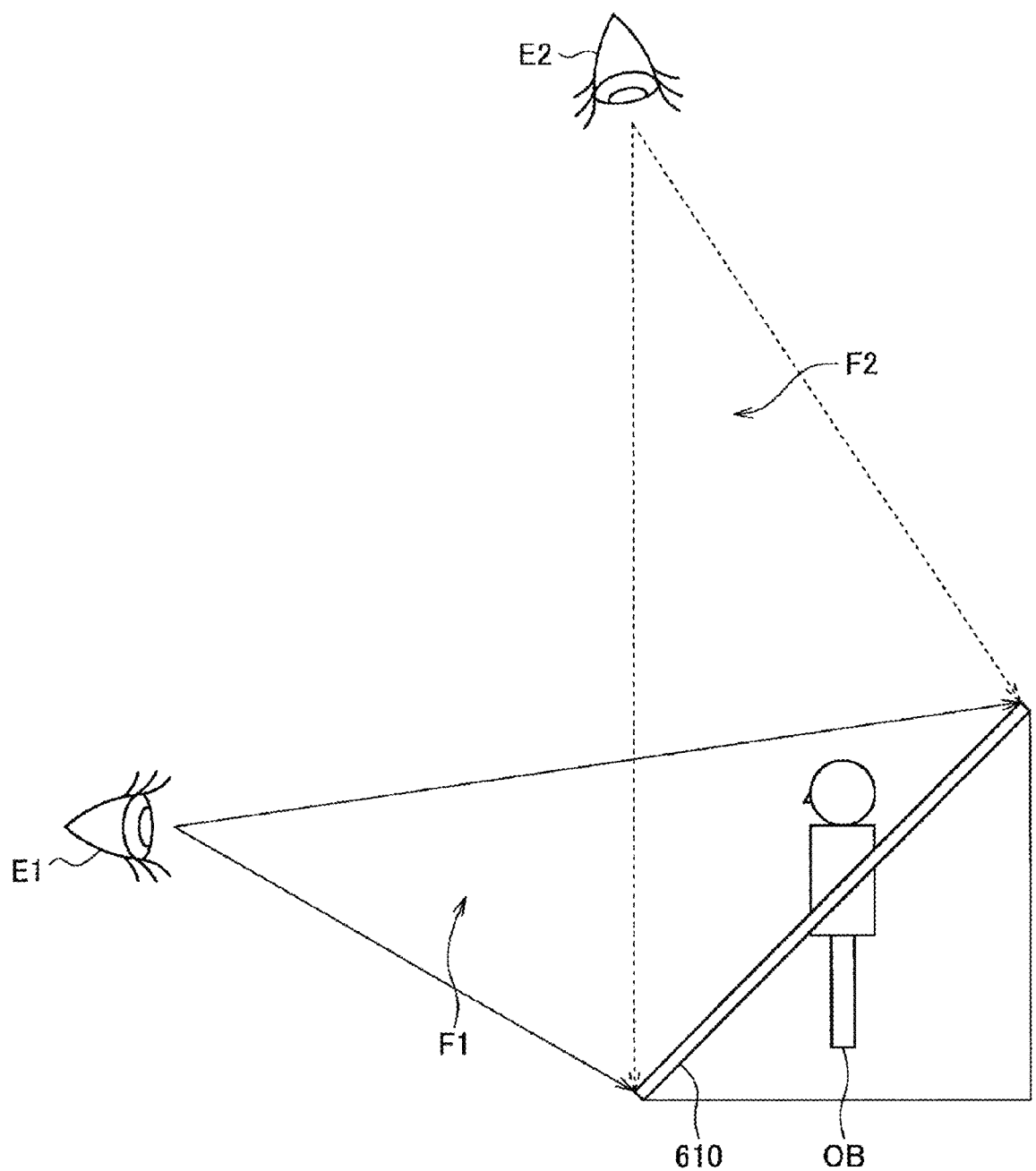
FIG. 7 is an explanatory diagram illustrating an example of stereoscopic display by the display unit according to the present embodiment.

With such a configuration, it is possible to further give a feeling of coexistence that the object OB exists in the same space as the user without making the user feel the display surface 610. In addition, by arranging the floor surface and the wall surface while suppressing the parallax amount as compared with the examples illustrated in FIGS. 4 to 6, it is possible to give a sufficient stereoscopic feeling and to suppress the burden on the user. Furthermore, as illustrated in FIG. 7, the object OB is included in the field of view F1 in a case where the user observes the object OB from a viewpoint E1, and the object OB is included in a field of view F2 in a case where the user observes the object OB from a viewpoint E2. Therefore, the user can observe the object OB from a wider viewpoint position.

As described above, the control unit 70 may display the object OB on the display unit 60 according to any one of the modes of FIGS. 4 to 7. Hereinafter, as an example, a case where the object OB is arranged so as to intersect the display surface 610 while standing upright with respect to the horizontal plane as illustrated in FIG. 7 will be described as an example.

(Control for Intuitive Observation)

Next, control for intuitive observation in the master slave system 1 will be described.

The control unit 70 according to the present embodiment calculates a first positional relationship between the eye of the user (observer) observing the object displayed on the display unit 60 and the first point in the master-side three-dimensional coordinate system, and controls the imaging unit 50 so that a second positional relationship between the imaging unit 50 that images the object and the second point corresponding to the first point in the slave-side three-dimensional coordinate system corresponds to the first positional relationship.

For example, the control unit 70 acquires information regarding the first observation direction of the eye of the user (observer) with respect to the first point in the master-side three-dimensional coordinate system, and controls the second observation direction so that the second observation direction of the imaging unit 50 with respect to the second point in the slave-side three-dimensional coordinate system corresponds to the first observation direction.

Here, the "second point" is a point serving as a reference for control of the imaging unit 50 in the slave-side three-dimensional coordinate system, and is also referred to as a "pivot point". For example, the second point can be any of one point of action (for example, the distal end portion of the contact portion 211 illustrated in FIG. 3, and the like) in the slave unit 20, a center point (for example, in a case where two slave units 20 illustrated in FIG. 3 are used, the center point or the like of the contact portion 211 of each slave unit 20) between two points of action in the slave unit 20, a point included in the object (for example, the center point or the like of the object), a focal point of the imaging unit 50, and a point included in an operation region of the slave unit 20 (for example, a center point or the like of the operation region of the slave unit 20). Note that the second point is not necessarily limited thereto.

The "first point" is a point corresponding to the second point (pivot point) in the master-side three-dimensional coordinate system. As illustrated in FIGS. 4 to 7, the first point can be set to any point in the master-side three-dimensional coordinate system as long as the point is within the field of view in which the user can observe the object.

For example, when the second point is the center point of the object, the first point coincides with the center point of the object displayed stereoscopically by the display unit 60. The same applies to a case where the second point is other than the center point of the object.

A control example of the imaging unit 50 by the control unit 70 will be described in detail with reference to FIGS. 8 to 11. Note that, in FIGS. 8 to 11, the object OB is simplified and represented by a straight line. FIGS. 8 to 11 illustrate an example in which the object OB and the first point P are set on the display surface 610, but as described above, these can be set at any positions in the field of view of the user.

FIG. 8 is a diagram when a state in which the user looks at the object OB displayed on the display surface 610 is viewed from the lateral direction (in a direction opposite to the X-axis direction). As illustrated in FIG. 8, in the YZ plane of the master-side three-dimensional coordinate system (XYZ coordinate system), an angle formed by a line G11 connecting the user's eye E and the first point P at a certain time T11 and the object OB is 90 degrees. At the subsequent time T12, it is assumed that the position of the user's eye E changes on the YZ plane in the master-side three-dimensional coordinate system. Specifically, it is assumed that an angle formed by a line G12 connecting the user's eye E and the first point P at the time T12 and the object OB changes to θ in the YZ plane.

With the change from the time T11 to the time T12, the control unit 70 controls the second observation direction so that the second observation direction of the imaging unit 50 with respect to the second point in the slave-side three-dimensional coordinate system (X'Y'Z' coordinate system) is substantially the same as the first observation direction (the observation direction of the user's eye E with respect to the first point P).

A specific description will be given with reference to FIG. 9. FIG. 9 is a diagram when a state in which the imaging unit 50 is imaging the object OB is viewed from the lateral direction (in a direction opposite to the X'-axis direction). As illustrated in FIG. 9, in the Y'Z' plane of the slave-side three-dimensional coordinate system (X'Y'Z' coordinate system), an angle formed by a line S11 connecting the imaging unit 50 and a second point P' at a certain time T11 and the object OB is 90 degrees, which is the same as the angle formed by the line G11 connecting the user's eye E and the first point P at the time T11 in FIG. 8 and the object OB. Furthermore, the length of the line S11 connecting the imaging unit 50 and the second point P' at the time T11 may be substantially the same as the length of the line G11 connecting the user's eye E and the first point P at the time T11 in FIG. 8.

At the subsequent time T12, the angle formed by the line S12 connecting the imaging unit 50 and the second point P' on the Y'Z' plane and the object OB is θ, which is the same as the angle formed by the line G12 connecting the user's eye E and the first point P at the time T12 in FIG. 8 and the object OB. Furthermore, the length of the line S12 connecting the imaging unit 50 and the second point P' at the time T12 may be substantially the same as the length of the line G12 connecting the user's eye E and the first point P at the time T12 in FIG. 8.

Figure 10:
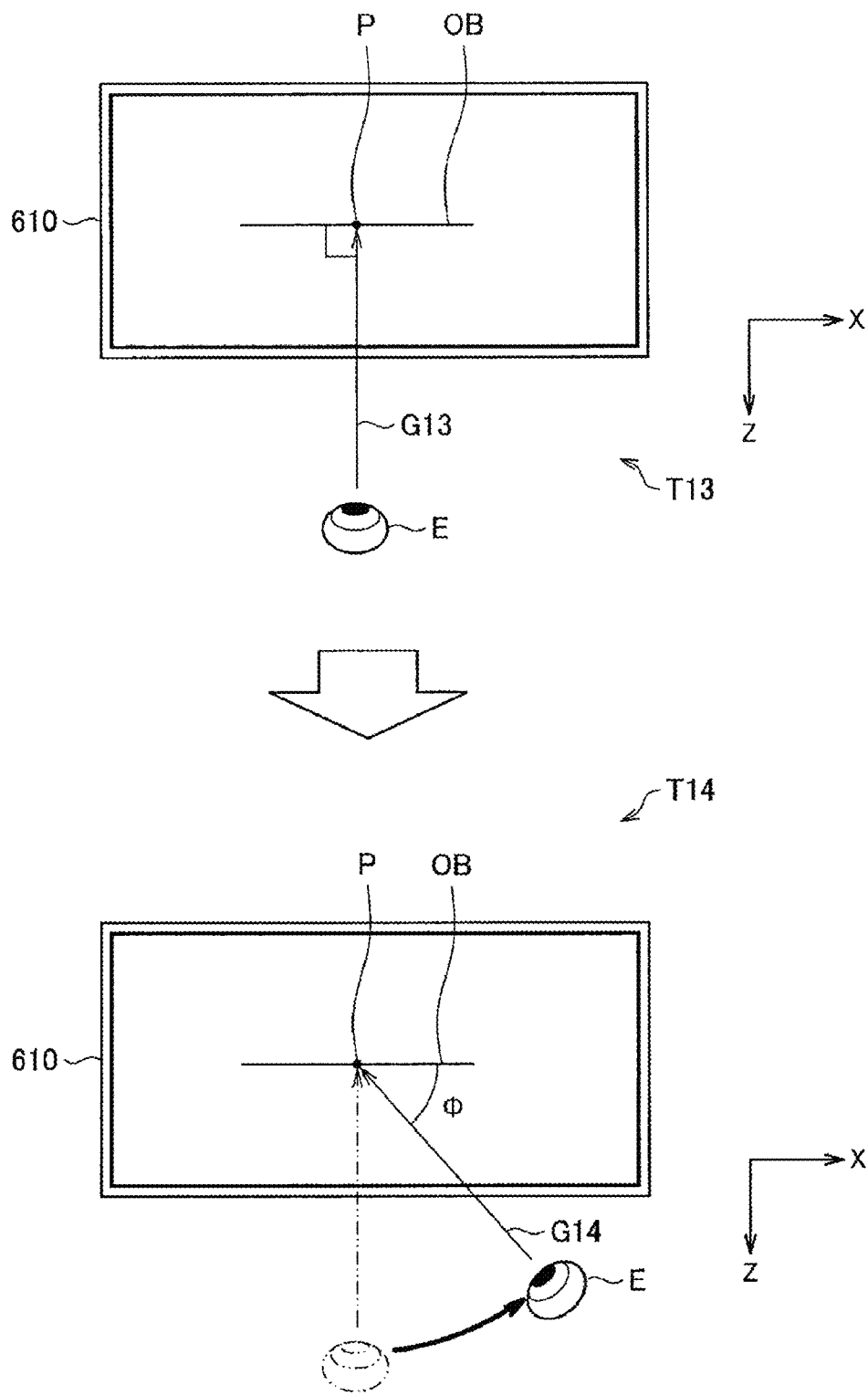
FIG. 10 is a diagram when a state in which the user looks at the object displayed on the display surface is viewed from above (in a direction opposite to a Y-axis direction).

The same applies to a case of being viewed from an angle different from the case of FIGS. 8 and 9. A specific description will be given with reference to FIGS. 10 and 11. FIG. 10 is a diagram when a state in which the user looks at the object OB displayed on the display surface 610 is viewed from above (in a direction opposite to the Y-axis direction). As illustrated in FIG. 10, in the XZ plane of the master-side three-dimensional coordinate system (XYZ coordinate system), an angle formed by a line G13 connecting the user's eye E and the first point P at a certain time T13 and the object OB is 90 degrees. At the subsequent time T14, it is assumed that the position of the user's eye E changes on the XZ plane in the master-side three-dimensional coordinate system. Specifically, it is assumed that an angle formed by a line G14 connecting the user's eye E and the first point P at the time T14 and the object OB changes to Φ in the XZ plane.

FIG. 11 is a diagram when a state in which the imaging unit 50 is imaging the object OB is viewed from above (in a direction opposite to the Y'-axis direction). As illustrated in FIG. 11, in the X'Z' plane of the slave-side three-dimensional coordinate system (X'Y'Z' coordinate system), an angle formed by a line S13 connecting the imaging unit 50 and the second point P' at a certain time T13 and the object OB is 90 degrees, which is the same as the angle formed by the line G13 connecting the user's eye E and the first point P at the time T13 in FIG. 10 and the object OB. Furthermore, the length of the line S13 connecting the imaging unit 50 and the second point P' at the time T13 may be substantially the same as the length of the line G13 connecting the user's eye E and the first point P at the time T13 in FIG. 10.

At the subsequent time T14, an angle formed by a line S14 connecting the imaging unit 50 and the second point P' on the X'Z' plane and the object OB is Φ, which is the same as the angle formed by the line G14 connecting the user's eye E and the first point P at the time T14 in FIG. 10 and the object OB. Furthermore, the length of the line S14 connecting the imaging unit 50 and the second point P' at the time T14 may be substantially the same as the length of the line G14 connecting the user's eye E and the first point P at the time T14 in FIG. 10.

For example, the control unit 70 analyzes the image acquired by the imaging unit 50 to detect the second point P' appearing in the image, and recognizes the position coordinates of the second point P' in the slave-side three-dimensional coordinate system and the direction from the imaging unit 50 to the second point P', thereby enabling the control as described with reference to FIGS. 8 to 11. As a result, the user can observe the object OB to look around from various directions of up, down, left, and right of the object OB by changing the position of the eye E (for example, even in a case where both hands are full for the operation of the master unit 10), so that the user can more intuitively observe the object OB.

(Control for Intuitive Operation)

Next, control for an intuitive operation in the master slave system 1 will be described.

As described above, in order to achieve an intuitive operation, control that does not generate Mental Rotation is required. Therefore, a condition under which the Mental Rotation does not occur will be described below.

A reference coordinate in the master-side three-dimensional coordinate system is defined as 0, a designated position coordinate of the master unit 10 is defined as M, a reference coordinate in the slave-side three-dimensional coordinate system is defined as 0', and a designated position coordinate of the slave unit 20 is defined as S, and the rotation matrix R is represented using these coordinates. For example, $_O{}^M r$ represents a rotation matrix from O to M, $_O{}^S R$ represents a rotation matrix from O' to S, and $_M{}^S R$ represents a rotation matrix from M to S. It can also be said that these rotation matrices R are offsets used for conversion of the three-dimensional coordinate system. In particular, the $_M{}^S R$ can also be said to be an offset used for conversion from the three-dimensional coordinate system for the master unit 10 to the three-dimensional coordinate system for the slave unit 20. In a case where the user performs input $V_M$ using the master unit 10, the input $V_M$ is converted into output $V_S$ of the slave unit 20 on the basis of the rotation matrix of the following Formula 1. $V_M$ and $V_S$ are vectors based on O and O', respectively.

[Math. 1]

$$_{O'}^{S}R \cdot V_S = {}_M^S R \cdot {}_O^M R \cdot V_M \qquad \text{Formula 1}$$

The condition that the Mental Rotation does not occur is that the operation direction of the slave unit 20 when the user operates the master unit 10 is substantially the same as the operation direction of the master unit 10 through coordinate conversion by the imaging unit 50 (for example, a camera) and the display unit 60 (for example, a display). That is, the condition that the Mental Rotation does not occur is that the following Formula 2 holds.

[Math. 2]

$$V_M = {}_M^O R \cdot {}_D^M R \cdot {}_C^D R \cdot {}_S^C R \cdot {}_{O'}^S R \cdot V_S \qquad \text{Formula 2}$$

Note that, in Formula 2, the designated position coordinate in the three-dimensional coordinate system for the imaging unit 50 (for example, a camera) is denoted by C, and the designated position coordinate in the three-dimensional coordinate system for the display unit 60 (for example, a display) is denoted by D. However, C and D are set so that the right and left, the up and down, and the normal direction of the imaging unit 50 coincide with the right and left, the up and down, and the normal direction of the display unit 60. In addition, ${}_S^C R$ represents a rotation matrix from S to C (offset used for conversion from three-dimensional coordinate system for slave unit 20 to three-dimensional coordinate system for imaging unit 50), ${}_C^D R$ represents a rotation matrix from C to D (offset used for conversion from three-dimensional coordinate system of image acquired by imaging unit 50 to three-dimensional coordinate system for display unit 60), and ${}_D^M R$ represents a rotation matrix from D to M (offset used for conversion from three-dimensional coordinate system for display unit 60 to three-dimensional coordinate system for master unit 10). In particular, ${}_C^E R$ represents conversion in a case where an image acquired by the imaging unit 50 is converted and displayed on the display unit 60, and becomes a unit matrix in a case where the image is not rotated at the time of conversion (in other words, in a case where only the change of the image magnification, the cutout of the image, or the like is performed).

When Formula 1 above is substituted into Formula 2, the following Formula 3 is obtained as a condition that the Mental Rotation does not occur. Here, I represents a unit matrix.

[Math. 3]

$$I = {}_D^M R \cdot {}_C^D R \cdot {}_S^C R \cdot {}_M^S R \qquad \text{Formula 3}$$

The control unit 70 controls the parameter while performing the control for intuitive observation described with reference to FIGS. 8 to 11 to satisfy the above Formula 3. Specifically, in a case where the control for intuitive observation described with reference to FIGS. 8 to 11 is performed, the position of the imaging unit 50 changes depending on the change in the position of the eye, and thus, the ${}_S^C R$ changes. The control unit 70 changes, for example, the ${}_C^D R$ or the ${}_M^S R$ in accordance with the change in the ${}_S^C R$ to satisfy Formula 3 (in other words, the control unit 70 dynamically changes the ${}_M^S R$, the ${}_S^C R$, or the ${}_C^E R$ by controlling the parameter). Note that the parameter controlled by the control unit 70 is only required to be any information that acts on each offset.

For example, in a case where only the ${}_C^D R$ is changed (in other words, in a case where the image is rotated by software processing), if the user's eye is not positioned in front of the rotated image, the stereoscopically displayed object is distorted, so that intuitive observation and intuitive operation are inhibited. In particular, when the display unit 60 is mounted on a stationary device, the positional relationship between the user's eye and the display unit 60 is not constant, which causes a problem. Therefore, the control unit 70 changes the position of the imaging unit 50 depending on the change in the position of the eye (that is, by changing the ${}_S^C R$,) by the control for the intuitive observation described with reference to FIGS. 8 to 11, thereby making the positional relationship between the rotated image and the user's eye appropriate. As a result, the control unit 70 can cause the user to visually recognize the stereoscopically displayed object without distortion, so that intuitive observation and intuitive operation can be achieved. In addition, physically rotating the display unit 60 (for example, a display) (that is, changing the ${}_D^M R$) is a large-scale operation and thus has a higher difficulty level. However, as described above, the control unit 70 can more easily achieve intuitive observation and intuitive operation by dynamically changing the ${}_M^S R$, the ${}_S^C R$, or the ${}_C^D R$. Note that, in a case where the control unit 70 can physically rotate the display unit 60 (for example, a display), the control unit 70 may dynamically change the ${}_D^M R$ by controlling a parameter. Furthermore, in a case where force feedback is performed on the master unit 10, the user can perceive the force in the same direction as the force applied to the slave unit 20 via the master unit 10.

(Control for Matching Gravity Direction)

Even if the occurrence of the Mental Rotation is prevented by the above processing, in a case where the first observation direction (the observation direction of the user's eye with respect to the first point) with respect to the gravity direction is different from the second observation direction (the observation direction of the imaging unit 50 with respect to the second point) with respect to the gravity direction, the apparent gravity direction when the user looks at the object OB displayed on the display unit 60 is different from the actual gravity direction.

Therefore, the control unit 70 may control the second observation direction so that the angle of the first observation direction with respect to the gravity direction and the angle of the second observation direction with respect to the gravity direction are substantially the same. For example, it is assumed that the direction opposite to the Y-axis direction in FIG. 8 and the direction opposite to the Y'-axis direction in FIG. 9 are the gravity direction. At this time, as illustrated in FIGS. 8 and 9, the second observation direction may be controlled so that the first observation direction with respect to the gravity direction and the second observation direction with respect to the gravity direction are 90 degrees each other at the time T11 and 8 each other at the time T12. As a result, the control unit 70 can make the apparent gravity direction and the actual gravity direction substantially the same when the user looks at the object OB displayed on the display unit 60. Furthermore, in a case where force feedback is performed on the master unit 10, in a case where the user grips an object using the slave unit 20, the user can perceive gravity applied to the object (direction and magnitude of gravity) via the master unit 10. Note that the offset in the horizontal direction may be appropriately changed (that is, the correspondence relationship between the XZ axis in FIG. 10 and the X'Z' axis in FIG. 11 may be appropriately changed.).

Furthermore, in a case where the angle of the first observation direction with respect to the gravity direction is different from the angle of the second observation direction with respect to the gravity direction, the control unit 70 may rotate the image by software processing by reflecting the rotation component in the gravity direction in the $_C{}^DR$ on the basis of the difference between these angles.

This will be described with reference to FIGS. 12 and 13. A of FIG. 12 is a diagram of a state in which the imaging unit 50 images the object OB as viewed from the lateral direction (in a direction opposite to the X'-axis direction). In addition, it is assumed that the direction opposite to the Y'-axis direction is the gravity direction. Further, it is assumed that the object OB is a doll, and the second point P' is set on the head of the object OB. At this time, it is assumed that the angle of the second observation direction (the observation direction of the imaging unit 50 with respect to the second point) with respect to the gravity direction is θ. B of FIG. 12 is a diagram illustrating an image V acquired by the imaging unit 50 in the state of A of FIG. 12.

Figure 13:
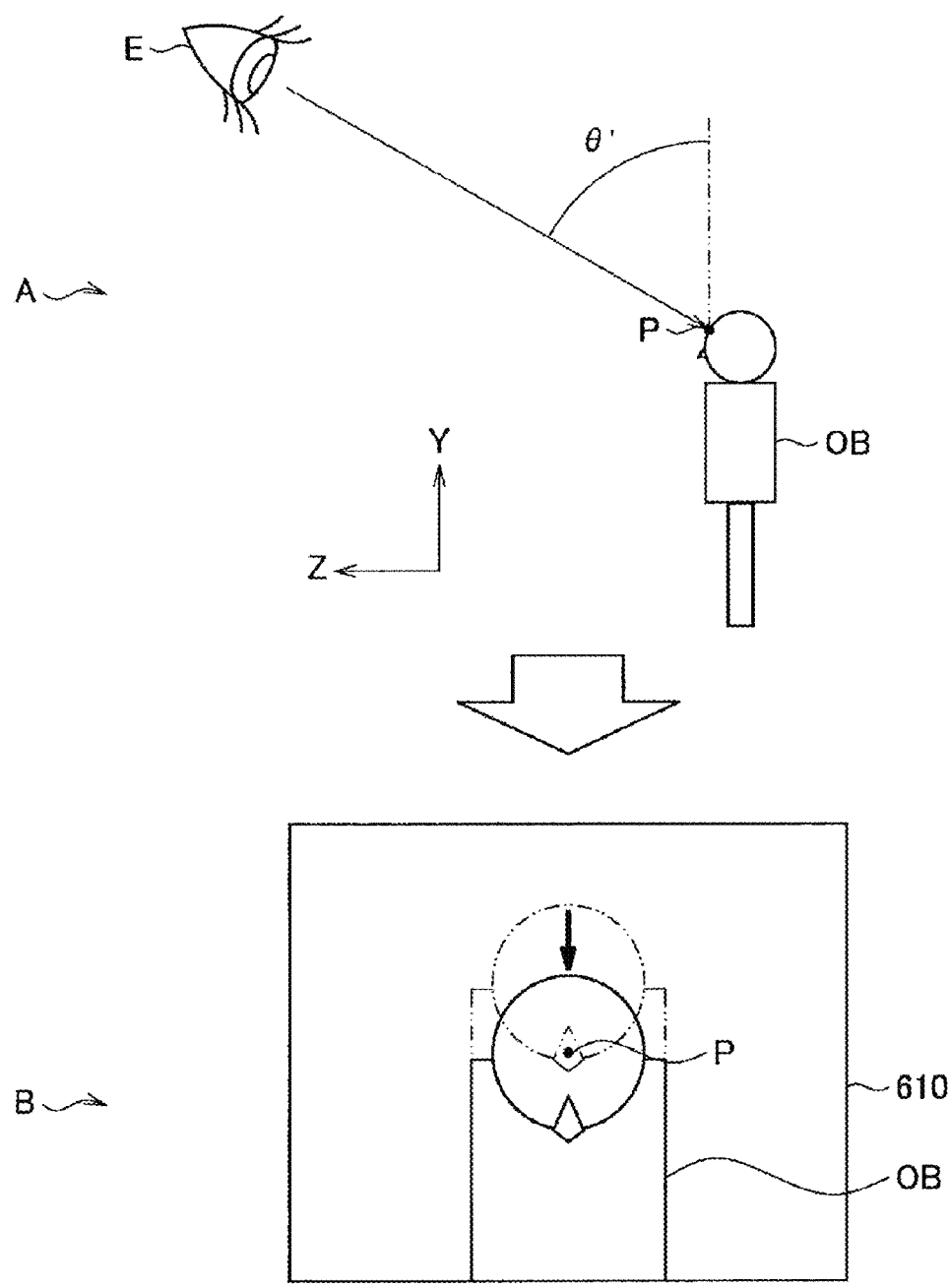
FIG. 13 is a diagram for explaining a coping method in a case where an angle of the first observation direction with respect to the gravity direction is different from an angle of the second observation direction with respect to the gravity direction.

B of FIG. 13 is a diagram when a state in which the user looks at the object OB displayed on the display surface 610 is viewed from the lateral direction (in a direction opposite to the X-axis direction) (the display surface 610 is omitted for convenience). In addition, it is assumed that the direction opposite to the Y-axis direction is the gravity direction. Further, similarly to FIG. 12, it is assumed that the object OB is a doll, and the first point P corresponding to the second point P' is set on the head of the object OB. At this time, it is assumed that the angle of the first observation direction (the observation direction of the user's eye E with respect to the first point P) with respect to the gravity direction is θ' different from θ.

In this case, the control unit 70 rotates the image V acquired by the imaging unit 50 around the X axis by software processing. B of FIG. 13 is a diagram illustrating an image displayed on the display surface 610 by the control of the control unit 70, and by the processing, the stereoscopic image of the object OB displayed on the display surface 610 is apparently compressed in the gravity direction more than the stereoscopic image of the object OB before processing. As described above, although distortion occurs in the stereoscopic image, the control unit 70 can make the apparent gravity direction and the actual gravity direction substantially the same by the processing.

(2.3. Configuration Example of Control Unit)

The control example by the control unit 70 according to the present embodiment has been described above. Next, a configuration example of the control unit 70 according to the present embodiment will be described with reference to FIG. 14.

Figure 14:
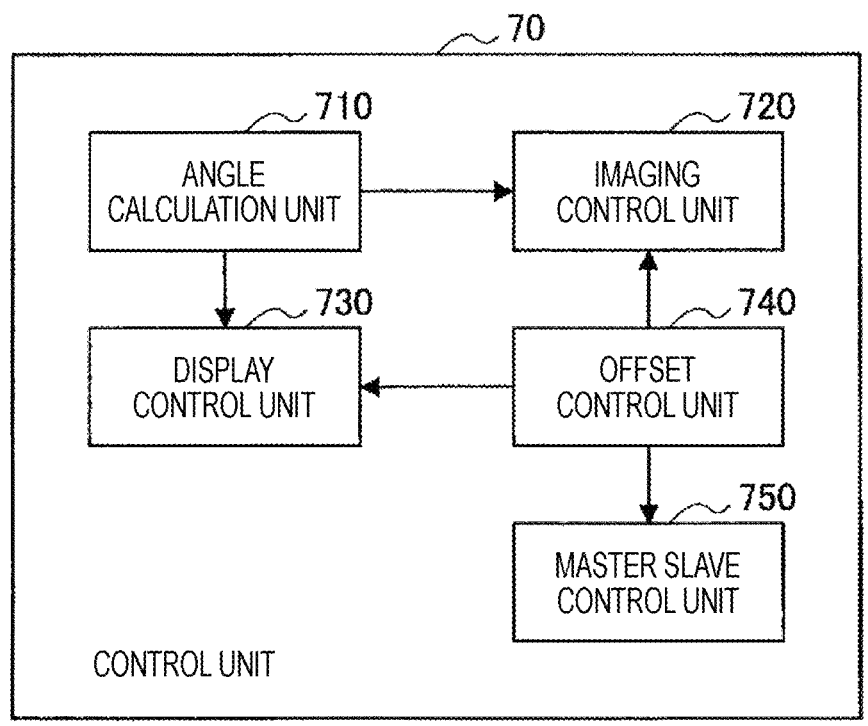
FIG. 14 is a block diagram illustrating a configuration example of a control unit according to the present embodiment.

FIG. 14 is a block diagram illustrating a configuration example of the control unit 70 according to the present embodiment. As illustrated in FIG. 14, the control unit 70 includes an angle calculation unit 710, an imaging control unit 720, a display control unit 730, an offset control unit 740, and a master slave control unit 750.

The angle calculation unit 710 is configured to calculate an angle formed by a line connecting the user's eye and the first point and the object. Specifically, in a case where the detection unit 30 detects the user's eye, the angle calculation unit 710 recognizes the position coordinates of the user's eye in the master-side three-dimensional coordinate system on the basis of the detection information provided from the detection unit 30. Then, the angle calculation unit 710 calculates an angle formed by a line connecting the user's eye and the first point and the object. For example, the angle calculation unit 710 calculates the angles formed by the lines G11 and G12 connecting the user's eye E and the first point P and the object OB on the YZ plane of the master-side three-dimensional coordinate system (XYZ coordinate system) as illustrated in FIG. 8, and the angles formed by the lines G13 and G14 connecting the user's eye E and the first point P and the object OB on the XZ plane as illustrated in FIG. 10. Then, the angle calculation unit 710 provides information regarding the angle (hereinafter, referred to as angle information) to the imaging control unit 720 and the display control unit 730. It should be noted that the angle information may be used as information regarding the first observation direction.

The imaging control unit 720 is configured to control imaging by the imaging unit 50 (for example, a camera). For example, the imaging control unit 720 controls the arm 40 supporting the imaging unit 50 on the basis of the angle information provided from the angle calculation unit 710 to control the second observation direction. Specifically, as described with reference to FIGS. 8 to 11, the imaging control unit 720 controls the arm 40 so that the first positional relationship between the user's eye and the first point in the master-side three-dimensional coordinate system corresponds to the second positional relationship between the imaging unit 50 and the second point in the slave-side three-dimensional coordinate system. In a case where the arm 40 has one or two or more joints and a link connected to the joint, the imaging control unit 720 calculates each joint angle by performing inverse kinematics calculation or the like. The imaging control unit 720 controls the arm 40 by providing information regarding the calculated joint angle and the like to the arm 40. As the arm 40 is controlled and the second observation direction changes, the $_S{}^CR$, which is a type of offset described above, changes.

Furthermore, in a case where information regarding the offset (hereinafter, referred to as offset information) is provided from the offset control unit 740 to be described later, the imaging control unit 720 may control the $_S{}^CR$ on the basis of the offset information. Note that the control contents by the imaging control unit 720 are not limited thereto. For example, in a case where there is a margin in the depth of field, the imaging control unit 720 may change the position of the imaging unit 50 in the front-back direction with respect to the object to reproduce motion parallax in which as the imaging unit 50 approaches the object, the object looks larger.

The display control unit 730 is configured to control display contents of the display unit 60. Specifically, the display control unit 730 converts the image on the basis of the angle information provided from the angle calculation unit 710 so that the image acquired by imaging by the imaging unit 50 is an image when viewed from the position of the user's eye (for example, rotation conversion or the like). Accordingly, $_C{}^DR$, which is a type of offset described above, changes. Then, the display control unit 730 outputs the converted image to the display unit 60.

Furthermore, in a case where offset information is provided from the offset control unit 740 to be described later, the display control unit 730 may control the $_C{}^DR$ on the basis of the offset information. Note that the control contents by the display control unit 730 are not limited thereto. For example, in a case where the imaging unit 50 can acquire the depth information of the object, the display control unit 730 may reconstruct (simulate) the object using the depth information and output an image including the reconstructed object to the display unit 60. As a result, distortion of the image is eliminated, and more intuitive observation may be achieved. Furthermore, the display control unit 730 may appropriately enlarge or reduce an image acquired by imaging by the imaging unit 50 by changing the display magnification. When the display magnification is changed, distortion occurs in the stereoscopic image, but the imaging control unit 720 described above may eliminate or reduce the distortion by controlling the distance between the imaging unit 50 and the object depending on the display magnification.

The offset control unit 740 is configured to control each offset. Specifically, the offset control unit 740 holds two or more combinations for each offset ($_M^S R$, $_S^C R$, $_C^D R$, and $_D^M R$) that satisfy the above Formula 3 when the user's face (or eye) is at a predetermined position (for example, the front surface of the display unit 60 or the like). Then, the offset control unit 740 changes the combination for each offset depending on an input or the like (for example, input using a foot pedal, and the like) by the user. As a result, the user can change the angle of the imaging unit 50 while satisfying Formula 3 (that is, while preventing occurrence of Mental Rotation,) in a state where the face is at a predetermined position (for example, the front surface of the display unit 60 or the like) without moving the face. The offset control unit 740 provides the offset information to the imaging control unit 720, the display control unit 730, and the master slave control unit 750.

The master slave control unit 750 is configured to control the slave unit 20 on the basis of an input to the master unit 10 by the user. Specifically, the master slave control unit 750 controls the designated position of the slave unit 20 on the basis of the designated position of the master unit 10 specified on the basis of the information communicated by the master unit 10 and the offset ($_M^S R$) provided from the offset control unit 740.

Here, the master slave control unit 750 may control the slave unit 20 on the basis of the second point (pivot point). For example, the master slave control unit 750 may control the slave unit 20 so that the designated position of the slave unit 20 is restricted on the basis of the second point. Specifically, the master slave control unit 750 may control the slave unit 20 so that the designated position of the slave unit 20 moves toward the second point (for example, the center point or the like of the operation region of the slave unit 20). Note that, in a case where the master slave control unit 750 restricts the designated position of the slave unit 20 in this manner (although not necessarily limited to this case), the designated position of the master unit 10 may be similarly restricted. The master slave control unit 750 may control the master unit 10 and the slave unit 20 by bilateral control in which the second point and the master slave control information are combined. As a result, the correspondence relationship between the designated positions of the master unit 10 and the slave unit 20 is maintained, so that the user can easily perform the operation. Other contents may be similar to the control of the slave unit in the existing master slave system, and thus detailed description thereof will be omitted.

The configuration example of the control unit 70 has been described above. Note that the above configuration described with reference to FIG. 14 is merely an example, and the configuration of the control unit 70 is not limited to such an example. For example, the control unit 70 may not necessarily include all of the configurations illustrated in FIG. 14, or may include a configuration not illustrated in FIG. 14. Furthermore, the configuration of the control unit 70 can be flexibly modified depending on specifications and operations.

(2.4. Processing Flow Example of Each configuration)

Figure 15:
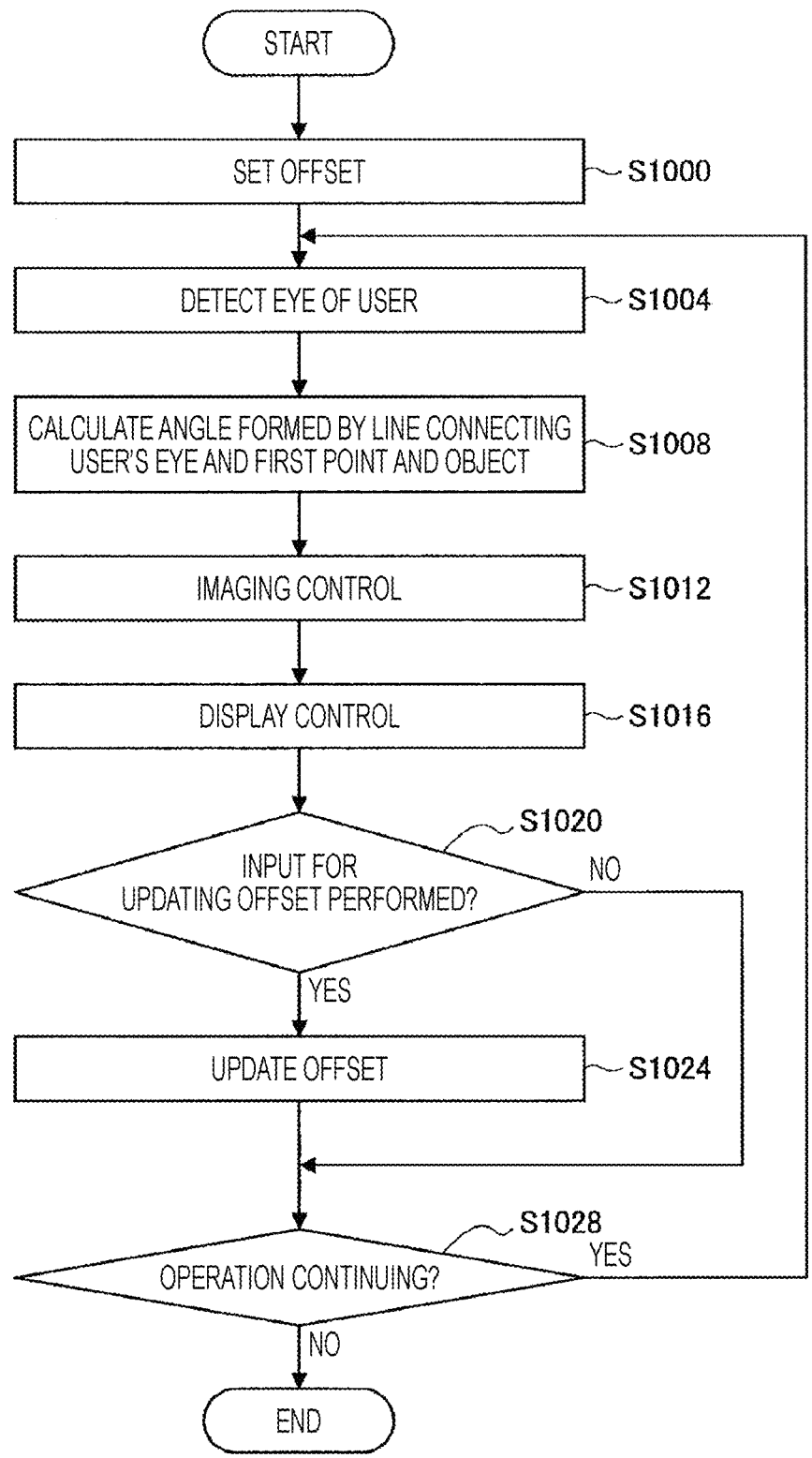
FIG. 15 is a flowchart illustrating a processing flow example of each configuration of the master slave system according to the present embodiment.

The configuration example of the control unit 70 according to the present embodiment has been described above. Next, a processing flow example of each configuration of the master slave system 1 according to the present embodiment will be described with reference to FIG. 15. FIG. 15 is a flowchart illustrating a processing flow example of each configuration of the master slave system 1 according to the present embodiment.

In step S1000, the offset control unit 740 sets each offset ($_M^S R$, $_S^C R$, $_C^D R$, and $_D^M R$). For example, the offset control unit 740 selects and sets one combination from two or more combinations for each offset in accordance with an input or the like by the user (for example, input using a foot pedal, and the like).

In step S1004, the detection unit 30 detects the user's eye. For example, the detection unit 30 has an imaging function, and detects the user's eye appearing in an image by analyzing the image acquired by imaging.

In step S1008, the angle calculation unit 710 calculates the angle formed by a line connecting the user's eye and the first point and the object. For example, the angle calculation unit 710 calculates the angles formed by the lines G11 and G12 connecting the user's eye E and the first point P and the object OB on the YZ plane of the master-side three-dimensional coordinate system (XYZ coordinate system) as illustrated in FIG. 8, and the angles formed by the lines G13 and G14 connecting the user's eye E and the first point P and the object OB on the XZ plane as illustrated in FIG. 10. Then, the angle calculation unit 710 generates angle information on the basis of the calculation result and provides the angle information to the imaging control unit 720.

In step S1012, the imaging control unit 720 performs imaging control on the basis of the angle information provided from the angle calculation unit 710. Specifically, as described with reference to FIGS. 8 to 11, the imaging control unit 720 controls the arm 40 so that the first positional relationship between the user's eye and the first point in the master-side three-dimensional coordinate system corresponds to the second positional relationship between the imaging unit 50 and the second point in the slave-side three-dimensional coordinate system, thereby controlling the position and posture of the imaging unit 50.

In step S1016, the display control unit 730 performs display control. Specifically, the display control unit 730 converts an image acquired by imaging by the imaging unit 50 so that the image is an image when viewed from the position of the user's eye, and outputs the converted image to the display unit 60. As a result, an appropriate stereoscopic image when viewed from the position of the user's eye is displayed on the display unit 60.

If an input for updating the offset (for example, input using a foot pedal by the user, or the like) has been made (step S1020/Yes), the offset control unit 740 updates the offset in accordance with the input in step S1024. When the input for updating the offset is not performed (step S1020/No), the processing of step S1024 (offset update processing) is not performed.

Then, when the operation by the user is continuing (step S1028/Yes), the processing of steps S1004 to S1024 is repeatedly continued. When the operation by the user is not continuing (step S1028/No), a series of processing ends.

Note that each step in the flowchart described above is not necessarily processed in time series in the described order. That is, each step in the flowchart may be processed in an order different from the described order or may be processed in parallel.

(2.5. Hardware Configuration Example of Control Unit)

Figure 16:
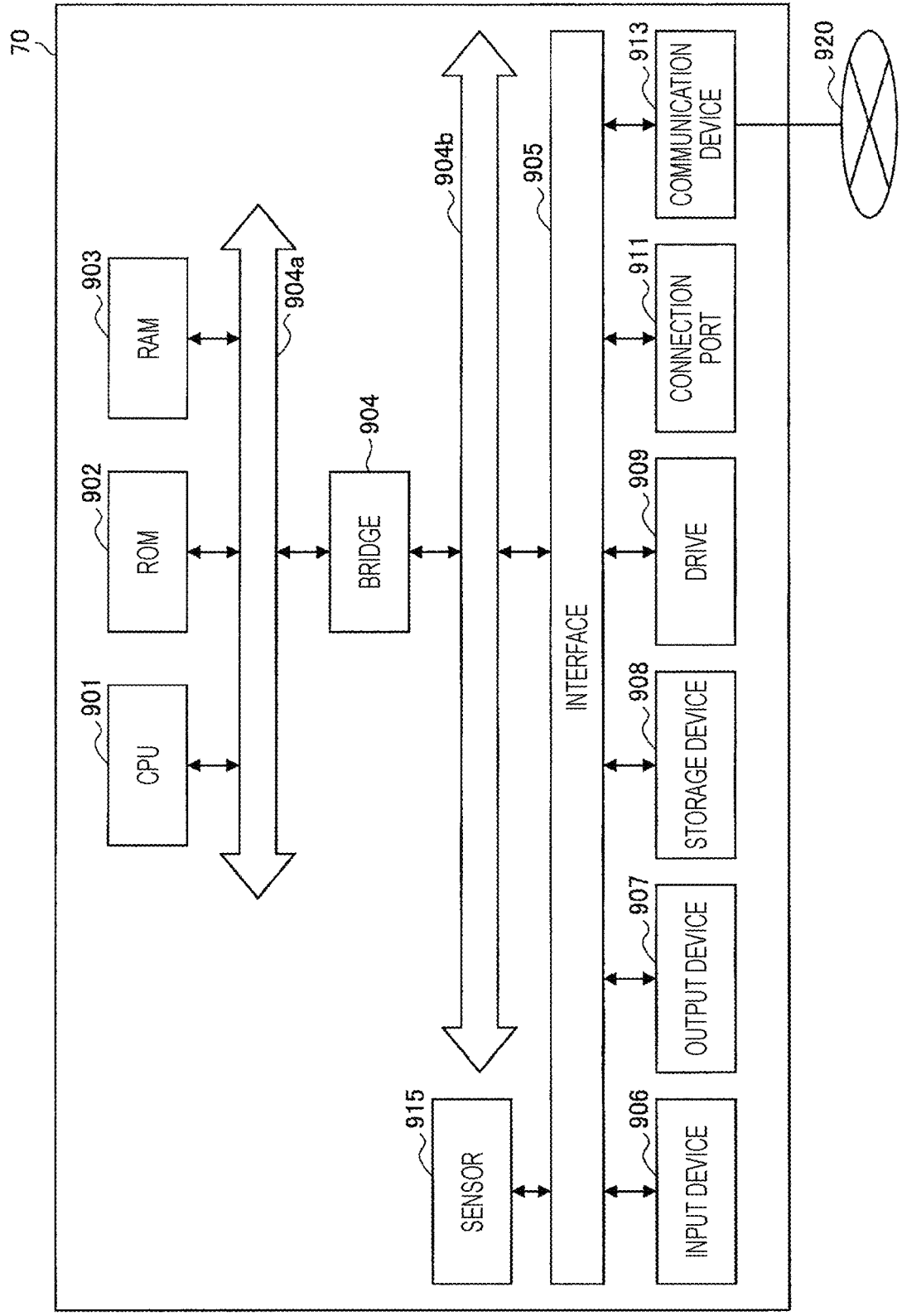
FIG. 16 is a block diagram illustrating a hardware configuration example of the control unit according to the present embodiment.

The processing flow example of each component of the master slave system 1 according to the present embodiment has been described above. Next, a hardware configuration example according to the present embodiment will be described with reference to FIG. 16. FIG. 16 is a block diagram illustrating a hardware configuration example of the control unit 70 according to the present embodiment. Information processing by the control unit 70 according to the present embodiment is achieved by cooperation of software and hardware described below.

As illustrated in FIG. 16, the control unit 70 includes a central processing unit (CPU) 901, a read only memory (ROM) 902, a random access memory (RAM) 903, and a host bus 904a. In addition, the control unit 70 includes a bridge 904, an external bus 904b, an interface 905, an input device 906, an output device 907, a storage device 908, a drive 909, a connection port 911, and a communication device 913. The control unit 70 may include a processing circuit such as a DSP or an ASIC instead of or in addition to the CPU 901.

The CPU 901 functions as an arithmetic processing device and a control device, and controls the overall operation in the control unit 70 according to various programs. Furthermore, the CPU 901 may be a microprocessor. The ROM 902 stores programs, operation parameters, and the like used by the CPU 901. The RAM 903 temporarily stores programs used in the execution of the CPU 901, parameters that appropriately change in the execution, and the like.

The CPU 901, the ROM 902, and the RAM 903 are mutually connected by a host bus 904a including a CPU bus and the like. The host bus 904a is connected to the external bus 904b such as a peripheral component interconnect/interface (PCI) bus via the bridge 904. Note that the host bus 904a, the bridge 904, and the external bus 904b do not necessarily need to be configured separately, and these functions may be implemented on one bus.

The input device 906 is implemented by, for example, a device to which information is input by the user, such as a mouse, a keyboard, a touch panel, a button, a microphone, a switch, and a lever. Furthermore, the input device 906 may be, for example, a remote control device using infrared rays or other radio waves, or may be an external connection device such as a mobile phone or a PDA corresponding to the operation of the control unit 70. Furthermore, the input device 906 may include, for example, an input control circuit or the like that generates an input signal on the basis of information input by the user using the above input means and outputs the input signal to the CPU 901. By operating the input device 906, the user can input various types of data to the control unit 70 and give an instruction on a processing operation.

The output device 907 includes a device capable of visually or aurally notifying the user of the acquired information. Examples of such a device include a display device such as a CRT display device, a liquid crystal display device, a plasma display device, an EL display device, and a lamp, an audio output device such as a speaker and a headphone, and a printer device. The output device 907 outputs, for example, results obtained by various processing performed by the control unit 70. Specifically, the display device visually displays results obtained by various processing performed by the control unit 70 in various formats such as text, images, tables, and graphs. On the other hand, the audio output device converts an audio signal including reproduced audio data, acoustic data, or the like into an analog signal and aurally outputs the analog signal.

The storage device 908 is a device for data storage formed as an example of a storage unit that can be included in the control unit 70. The storage device 908 is implemented by, for example, a magnetic storage device such as an HDD, a semiconductor storage device, an optical storage device, a magneto-optical storage device, or the like. The storage device 908 may include a storage medium, a recording device that records data in the storage medium, a reading device that reads data from the storage medium, a deletion device that deletes data recorded in the storage medium, and the like. The storage device 908 stores programs executed by the CPU 901, various data, various data acquired from the outside, and the like.

The drive 909 is a reader/writer for a storage medium, and is built in or externally attached to the control unit 70. The drive 909 reads information recorded in a removable storage medium such as a mounted magnetic disk, optical disk, magneto-optical disk, or semiconductor memory, and outputs the information to the RAM 903. Furthermore, the drive 909 can also write information to a removable storage medium.

The connection port 911 is an interface connected to an external device, and is a connection port to an external device capable of transmitting data by, for example, a universal serial bus (USB) or the like.

The communication device 913 is, for example, a communication interface formed by a communication device or the like for connecting to the network 920. The communication device 913 is, for example, a communication card for wired or wireless local area network (LAN), long term evolution (LTE), Bluetooth (registered trademark), wireless USB (WUSB), or the like. Furthermore, the communication device 913 may be a router for optical communication, a router for asymmetric digital subscriber line (ADSL), a modem for various communications, or the like. For example, the communication device 913 can transmit and receive signals and the like to and from the Internet and other communication devices according to a predetermined protocol such as TCP/IP.

Note that the network 920 is a wired or wireless transmission path of information transmitted from a device connected to the network 920. For example, the network 920 may include a public network such as the Internet, a telephone network, or a satellite communication network, various local area networks (LANs) including Ethernet (registered trademark), a wide area network (WAN), or the like. Furthermore, the network 920 may include a dedicated line network such as an Internet protocol-virtual private network (IP-VPN).

The hardware configuration example capable of implementing the function of the control unit 70 according to the present embodiment has been described above. Each of the above-described components may be implemented using a general-purpose member, or may be implemented by hardware specialized for the function of each component. Therefore, it is possible to appropriately change the hardware configuration to be used depending on the technical level at the time of carrying out the present embodiment.

Note that a computer program for implementing each function of the control unit 70 according to the present embodiment as described above can be created and mounted on a PC or the like. Furthermore, a computer-readable recording medium storing such a computer program can also be provided. The recording medium is, for example, a magnetic disk, an optical disk, a magneto-optical disk, a flash memory, or the like. Furthermore, the computer program described above may be distributed via, for example, a network without using a recording medium.

3. CONCLUSION

As described above, the control device according to the present embodiment calculates the first positional relationship between the eye of the user (observer) observing the object displayed on the display unit 60 and the first point in the master-side three-dimensional coordinate system, and controls the imaging unit 50 so that the second positional relationship between the imaging unit 50 that images the object and the second point corresponding to the first point in the slave-side three-dimensional coordinate system corresponds to the first positional relationship. As a result, the user can observe the object to look around from various directions of up, down, left, and right of the object by changing the position of the eye, so that the user can more intuitively observe the object.

In addition, the control device according to the present embodiment prevents the occurrence of Mental Rotation by controlling the parameter to satisfy Formula 3 described above. As a result, the user can perform an intuitive operation.

Although the preferred embodiments of the present disclosure have been described in detail with reference to the accompanying drawings, the technical scope of the present disclosure is not limited to such examples. It is obvious that a person having ordinary knowledge in the technical field of the present disclosure can conceive various change examples or modification examples within the scope of the technical idea described in the claims, and it is naturally understood that these also belong to the technical scope of the present disclosure.

Furthermore, the effects described in the present specification are merely illustrative or exemplary, and are not restrictive. That is, the technology according to the present disclosure can exhibit other effects obvious to those skilled in the art from the description of the present specification together with or instead of the above effects.

Note that the following configurations also belong to the technical scope of the present disclosure.

(1)

A control device including a control unit that:

calculates a first positional relationship between an eye of an observer observing an object displayed on a display unit and a first point in a master-side three-dimensional coordinate system; and controls an imaging unit that images the object so that a second positional relationship between the imaging unit and a second point corresponding to the first point in a slave-side three-dimensional coordinate system corresponds to the first positional relationship.

(2)

The control device according to (1), in which the control unit:

acquires information regarding a first observation direction of the eye of the observer with respect to the first point in the master-side three-dimensional coordinate system; and controls a second observation direction of the imaging unit with respect to the second point so that the second observation direction corresponds to the first observation direction in the slave-side three-dimensional coordinate system.

(3)

The control device according to (2), in which the control unit controls the second observation direction so that the second observation direction and the first observation direction are substantially the same.

(4)

The control device according to (3), in which the control unit controls the second observation direction so that an angle of the first observation direction with respect to a gravity direction and an angle of the second observation direction with respect to the gravity direction are substantially the same.

(5)

The control device according to any one of (2) to (4), in which the control unit controls the second observation direction by controlling an arm supporting the imaging unit.

(6)

The control device according to any one of (2) to (5), in which the control unit controls a parameter to satisfy Formula 4 when ${}_M^S R$ is a rotation matrix used for conversion from a three-dimensional coordinate system for a master unit that receives an input from the observer to a three-dimensional coordinate system for a slave unit controlled on the basis of the input, ${}_S^C R$ is a rotation matrix used for conversion from the three-dimensional coordinate system for the slave unit to the three-dimensional coordinate system for the imaging unit, ${}_C^D R$ is a rotation matrix used for conversion from the three-dimensional coordinate system for the imaging unit to the three-dimensional coordinate system for the display unit, ${}_D^M R$ is a rotation matrix used for conversion from the three-dimensional coordinate system for the display unit to the three-dimensional coordinate system for the master unit, and I is a unit matrix.

[Math. 4]

$$I = {}_D^M R \cdot {}_C^D R \cdot {}_S^C R \cdot {}_M^S R \qquad \text{Formula 4}$$

(7)

The control device according to (6), in which the control unit dynamically changes the ${}_M^S R$, the ${}_S^C R$, or the ${}_C^D R$ by controlling a parameter.

(8)

The control device according to (6) or (7), in which the control unit reflects a rotation component in the gravity direction in the ${}_C^D R$ on the basis of a difference between an angle of the first observation direction with respect to a gravity direction and an angle of the second observation direction with respect to the gravity direction.

(9)

The control device according to any one of (1) to (8), in which the second point is any one of one point of action in a slave unit, a center point between two points of action in the slave unit, a point included in the object, an in-focus point of the imaging unit, and a point included in an operation region of the slave unit.

(10)

The control device according to any one of (1) to (9), in which the control unit controls a slave unit on the basis of the second point.

(11)

The control device according to any one of (1) to (10), in which the display unit is mounted on a stationary device.

(12)

The control device according to any one of (1) to (11), in which a space on the slave side is a real space or a virtual space.

(13)

A master slave system including:

a slave unit;

a master unit used to operate the slave unit; and a control unit that calculates a first positional relationship between an eye of an observer observing an object displayed on a display unit and a first point in a master-side three-dimensional coordinate system, and controls an imaging unit that images the object so that a second positional relationship between the imaging unit and a second point corresponding to the first point in a slave-side three-dimensional coordinate system corresponds to the first positional relationship.

REFERENCE SIGNS LIST

1 Master slave system
10 Master unit
20 Slave unit
30 Detection unit
40 Arm
50 Imaging unit
60 Display unit
610 Display surface
70 Control unit
710 Angle calculation unit
720 Imaging control unit
730 Display control unit
740 Offset control unit
750 Master slave control unit

The invention claimed is:

1. A control device comprising:

control circuitry that calculates a first positional relationship between an eye of an observer observing an object displayed on a display and a first point in a master-side three-dimensional coordinate system; and controls an imaging device with optics that images the object so that a second positional relationship between the imaging device and a second point corresponding to the first point in a slave-side three-dimensional coordinate system corresponds to the first positional relationship, wherein the control circuitry controls a parameter to satisfy $$I = {}^M_D R \cdot {}^D_C R \cdot {}^C_S R \cdot {}^S_M R$$

under a condition ${}^S_M R$ is a rotation matrix used for conversion from a three-dimensional coordinate system for a master device that receives an input from the observer to a three-dimensional coordinate system for a slave device controlled on a basis of the input, ${}^C_S R$ is a rotation matrix used for conversion from the three-dimensional coordinate system for the slave device to a three-dimensional coordinate system for the imaging device, ${}^D_C R$ is a rotation matrix used for conversion from the three-dimensional coordinate system for the imaging device to a three-dimensional coordinate system for the display, ${}^M_D R$ is a rotation matrix used for conversion from the three-dimensional coordinate system for the display to the three-dimensional coordinate system for the master device, and I is a unit matrix.

2. The control device according to claim 1, wherein the control circuitry:

acquires information regarding a first observation direction of the eye of the observer with respect to the first point in the master-side three-dimensional coordinate system; and controls a second observation direction of the imaging device with respect to the second point so that the second observation direction corresponds to the first observation direction in the slave-side three-dimensional coordinate system.

3. The control device according to claim 2, wherein the control circuitry controls the second observation direction so that the second observation direction and the first observation direction are substantially the same.

4. The control device according to claim 3, wherein the control circuitry controls the second observation direction so that an angle of the first observation direction with respect to a gravity direction and an angle of the second observation direction with respect to the gravity direction are substantially the same.

5. The control device according to claim 2, wherein the control circuitry controls the second observation direction by controlling an arm supporting the imaging device.

6. The control device according to claim 1, wherein the control circuitry dynamically changes the ${}^S_M R$, the ${}^C_S R$, or the ${}^D_C R$ by controlling a parameter.

7. The control device according to claim 1, wherein the control circuitry reflects a rotation component in the gravity direction in the ${}^D_C R$ on a basis of a difference between an angle of the first observation direction with respect to a gravity direction and an angle of the second observation direction with respect to the gravity direction.

8. The control device according to claim 1, wherein the second point is any one of one point of action in a slave device, a center point between two points of action in the slave device, a point included in the object, an in-focus point of the imaging device, and a point included in an operation region of the slave device.

9. The control device according to claim 1, wherein the control circuitry controls a slave device on a basis of the second point.

10. The control device according to claim 1, wherein the display is mounted on a stationary device.

11. The control device according to claim 1, wherein a space on the slave side is a real space or a virtual space.

12. A master slave system comprising:

a slave device;

a master device used to operate the slave device; and control circuitry that calculates a first positional relationship between an eye of an observer observing an object displayed on a display and a first point in a master-side three-dimensional coordinate system, and controls an imaging device with optics that images the object so that a second positional relationship between the imaging device and a second point corresponding to the first point in a slave-side three-dimensional coordinate system corresponds to the first positional relationship, wherein
the control circuitry controls a parameter to satisfy $$I = {}^{M}_{D}R \cdot {}^{D}_{C}R \cdot {}^{C}_{S}R \cdot {}^{S}_{M}R$$

under a condition ${}^{S}_{M}R$ is a rotation matrix used for conversion from a three-dimensional coordinate system for the master device that receives an input from the observer to a three-dimensional coordinate system for the slave device controlled on a basis of the input, ${}^{C}_{S}R$ is a rotation matrix used for conversion from the three-dimensional coordinate system for the slave device to a three-dimensional coordinate system for the imaging device, ${}^{D}_{C}R$ is a rotation matrix used for conversion from the three-dimensional coordinate system for the imaging device to a three-dimensional coordinate system for the display, ${}^{M}_{D}R$ is a rotation matrix used for conversion from the three-dimensional coordinate system for the display to the three-dimensional coordinate system for the master device, and I is a unit matrix.

\* \* \* \* \*